US012213984B2

(12) United States Patent
Fukui et al.

(10) Patent No.: US 12,213,984 B2
(45) Date of Patent: Feb. 4, 2025

(54) IMMUNOREGULATORY AGENT

(71) Applicant: KYUSHU UNIVERSITY, NATIONAL UNIVERSITY CORPORATION, Fukuoka (JP)

(72) Inventors: Yoshinori Fukui, Fukuoka (JP); Takehito Uruno, Fukuoka (JP); Yuki Sugiura, Tokyo (JP)

(73) Assignee: KYUSHU UNIVERSITY, NATIONAL UNIVERSITY CORPORATION, Fukuoka (JP)

( * ) Notice: Subject to any disclaimer, the term of this patent is extended or adjusted under 35 U.S.C. 154(b) by 284 days.

(21) Appl. No.: 17/521,335

(22) Filed: Nov. 8, 2021

(65) Prior Publication Data
US 2022/0054506 A1 Feb. 24, 2022

Related U.S. Application Data

(62) Division of application No. 15/775,895, filed as application No. PCT/JP2016/084259 on Nov. 18, 2016, now Pat. No. 11,395,826.

(30) Foreign Application Priority Data

Nov. 20, 2015 (JP) ................................. 2015-228190

(51) Int. Cl.
| | | |
|---|---|---|
| A61K 31/575 | (2006.01) | |
| A61K 31/7088 | (2006.01) | |
| A61K 31/713 | (2006.01) | |
| A61K 35/76 | (2015.01) | |
| A61K 38/00 | (2006.01) | |
| A61K 45/00 | (2006.01) | |
| A61K 45/06 | (2006.01) | |
| A61K 48/00 | (2006.01) | |
| A61P 37/06 | (2006.01) | |
| C07K 14/47 | (2006.01) | |

(52) U.S. Cl.
CPC ........ *A61K 31/575* (2013.01); *A61K 31/7088* (2013.01); *A61K 31/713* (2013.01); *A61K 35/76* (2013.01); *A61K 38/00* (2013.01); *A61K 45/00* (2013.01); *A61K 45/06* (2013.01); *A61K 48/00* (2013.01); *A61P 37/06* (2018.01); *C07K 14/47* (2013.01)

(58) Field of Classification Search
None
See application file for complete search history.

(56) References Cited

U.S. PATENT DOCUMENTS

| | | | | |
|---|---|---|---|---|
| 5,053,406 A | * | 10/1991 | Srnka | ............... A61K 31/575 514/182 |
| 2002/0098207 A1 | * | 7/2002 | Maes | ............... A61K 8/63 424/400 |
| 2003/0105000 A1 | * | 6/2003 | Pero | ............... C07K 1/047 514/19.3 |
| 2007/0031844 A1 | * | 2/2007 | Khvorova | ............... A61P 3/10 435/6.13 |
| 2007/0202077 A1 | | 8/2007 | Brodsky et al. | |

FOREIGN PATENT DOCUMENTS

| | | |
|---|---|---|
| JP | 2007-297289 A | 11/2007 |
| JP | 2009-528334 A | 8/2009 |
| WO | 2007/099304 A1 | 9/2007 |
| WO | 2011/077245 A2 | 6/2011 |
| WO | 2012/157389 A1 | 11/2012 |
| WO | 2014/178427 A1 | 11/2014 |
| WO | 2015/100312 A1 | 7/2015 |

OTHER PUBLICATIONS

Bowie et al (Science, 1990, 247:1306-1310) (Year: 1990).*
Ibragimova and Wade (Biophysical Journal, Oct. 1999, vol. 77, pp. 2191-2198) (Year: 1999).*
Burgess et al (J of Cell Bio. 111:2129-2138, 1990) (Year: 1990).*
Lazar et al (Molecular and Cellular Biology, 1988, 8:1247-1252) (Year: 1980).*
Pearson, W.R. (2015. Curr. Protoc. Bioinform. 51:4. 12.1-4. 12.8 doi: 10.1002/0471250953.bi0412s51) (Year: 2015).*
Meloche et al. (J. Steroid Biochemistry & Mol. Biology 2001 77: 261-269) (Year: 2001).*
Gura (Science, 1995, 270:575-577) (Year: 1995).*
Wang et al. (Expert Opin. Biol. Ther. 2009 9(1)): 1357-1368) (Year: 2009).*
Khan et al. (Expert Opinion On Drug Delivery, 2023 20 (9): 1167-1187) (Year: 2023).*
Niederkorn J. Y., "See no evil, hear no evil, do no evil: the lessons of immune privilege". Nat Immunol, 7 (4), pp. 354-359, 2006.
Joyce J. A and Fearon D. T., "T cell exclusion, immune privilege, and the tumor microenvironment". Science, 348 (6230), pp. 74-80, 2015.
Aleksandrov D. A. et al., "Cholesterol and its anionic derivatives inhibit 5-lipoxygenase activation in polymorphonuclear leukocytes and MonoMac6 cells". FEBS Journal, vol. 273, No. 3, pp. 548-557, 2006, ISSN: 1742-464X.
Kawakami F. et al., "The effects of cholesterol-3-sulfate (CH-3S) on the phosphorylation of human C3a (hC3a) in vitro and on the ability of hC3a to induce vascular permeability in rats". Biological and Pharmaceutical Bulletin, vol. 27, No. 3, pp. 282-287, 2004, ISSN: 0918-6158.
Villablanca E. J. et al., "Tumor-mediated liver X receptor-α activation inhibits CC chemokine receptor-7 expression on dendritic cells and dampens antitumor responses". Nature Medicine, vol. 16, No. 1, pp. 98-105, 2010, ISSN: 1078-8956.
Suitters A. J. et al., "Immune enhancing effects of dehydroepiandrosterone and dehydroepiandrosterone sulphate and the role of steriod sulphatase". Immunology, vol. 91, No. 2, pp. 314-321, 1997, ISSN: 0019-2805.

(Continued)

*Primary Examiner* — Peter J Reddig
(74) *Attorney, Agent, or Firm* — Oliff PLC

(57) ABSTRACT

An immunoregulatory agent containing a regulatory agent that regulates Dedicator of cytokinesis 2 (DOCK2)-mediated Rac activation as an active ingredient is provided.

9 Claims, 19 Drawing Sheets

Specification includes a Sequence Listing.

(56) References Cited

OTHER PUBLICATIONS

Uruno et al., "Men' eki Yokuseizai Kaihatsu no Atarashii Bunshi Hyoteki to shite no DOCK2". Experimental Medicine, vol. 32, No. 2, pp. 330-335, 2014, ISSN: 0288-5514.

Nishikimi A. et al., "Blockade of inflammatory responses by a small-molecule inhibitor of the Rac activator DOCK2". Chemistry and Biology, vol. 19, No. 4, pp. 488-497, 2012, ISSN: 1074-5521.

Terasawa M. et al., "Dimerization of DOCK2 is essential for DOCK2-mediated Rac activation and lymphocyte migration". PLOS One, vol. 7, issue. 9, e46277, pp. 1-7, 2012, ISSN: 1932-6203.

Tolias K. F. et al., "The Rac1-GEF Tiam1 couples the NMDA receptor to the activity-dependent development of dendritic arbors and spines". Neuron, vol. 45, No. 4, pp. 525-538, 2005, ISSN: 0896-6273.

Gonzalez E. et al., "Rac1 modulates sphingosine 1-phosphate-mediated activation of phosphoinositide 3-kinase/Akt signaling pathways in vascular endothelial cells". Journal of Biological Chemistry, vol. 281, No. 6, pp. 3210-3216, 2006, ISSN: 0021-9258.

Worthylake D. K. et al., "Crystal structure of Rac1 in complex with the guanine nucleotide exchange region of Tiam1". Nature, vol. 408, pp. 682-688, 2000, ISSN: 0028-0836.

Ma A. D. et al., "Cytoskeletal reorganization by G protein-coupled receptors is dependent on phosphoinositide 3-kinase g, a Rac guanosine exchange factor, and Rac". Molecular and Cellular Biology, vol. 18, No. 8, pp. 4744-4751, 1998, ISSN: 0270-7306.

Kawakatsu T. et al., "Vav2 as a Rac-GDP/GTP exchange factor responsible for the nectin-induced, c-Src- and Cdc42-mediated activation of Rac". Journal of Biological Chemistry, vol. 280, No. 6, pp. 4940-4947, 2005, ISSN: 0021-9258.

Kodama A. et al., "Involvement of an SHP-2-Rho small G protein pathway in hepatocyte growth factor/scatter factor-induced cell scattering". Molecular Biology of the Cell, vol. 11, No. 8, pp. 2565-2575, 2000, ISSN: 1059-1524.

Thomas M. P. et al., "Discovery and Development of the Aryl o-Sulfamate Pharmacophore for Oncology and Women's Health". Journal of Medicinal Chemistry, vol. 58, No. 19, pp. 7634-7658, 2015, ISSN: 0022-2623.

Feb. 7, 2017 International Search Report issued in International Patent Application No. PCT/JP2016/084259.

Jul. 10, 2019 Extended Search Report issued in European Patent Application No. 16866436.5.

Wang et al., "Inhibition of T Cell Receptor Signaling by Cholesterol Sulfate, a Naturally Occurring Derivative of Membrane Cholesterol", Natural Immunology, vol. 17, No. 7, (Jul. 2016), pp. 844-850.

Sakurai, Tetsuya et al., "Cholesterol Sulfate is a DOCK2 Inhibitor That Mediates Tissue-Specific Immune Evasion in the Eye", Science Signaling, vol. 11, No. 541, (Jul. 2018), pp. 1-11.

Nov. 4, 2019 Office Action issued in U.S. Appl. No. 15/775,895.

Kunisaki et al. ("Kunisaki", J. Cell Biology, 2006, 174, 647-652) (Year: 2006).

Aug. 11, 2020 Office Action issued in U.S. Appl. No. 15/775,895.

Jul. 19, 2021 Office Action issued in U.S. Appl. No. 15/775,895.

Polacheck et al. (J. Clinical Microbiology 1992 30(12): 3290-3293) (Year: 1992).

Nov. 26, 2021 Office Action issued in U.S. Appl. No. 15/775,895.

Pappas et al. (Am. J. Transplantation 2009 9(Suppl4): S173-S179) (Year: 2009).

Shen, S. et al. "25-Hydroxycholesterol-3-Sulfate (25HC3S): a Physiological Ligand of PPARγ?," Gastroenterology, vol. 140, No. 5, pp. S-890, May 2011.

Apr. 22, 2022 Notice of Allowance issued in U.S. Appl. No. 15/775,895.

* cited by examiner

SEQUENCE LISTING

```
<160> NUMBER OF SEQ ID NOS: 17

<210> SEQ ID NO 1
<211> LENGTH: 427
<212> TYPE: PRT
<213> ORGANISM: Homo sapiens
<220> FEATURE:
<221> NAME/KEY: misc_feature
```

-continued

```
<223> OTHER INFORMATION: B lobe and C lobe of DHR-2 domain of human
      DOCK2
<220> FEATURE:
<221> NAME/KEY: misc_feature
<222> LOCATION: (1)..(141)
<223> OTHER INFORMATION: B lobe
<220> FEATURE:
<221> NAME/KEY: misc_feature
<222> LOCATION: (142)..(427)
<223> OTHER INFORMATION: C lobe

<400> SEQUENCE: 1

Ser Lys Asp Asn Arg Met Ser Cys Thr Val Asn Leu Leu Asn Phe Tyr
1               5                   10                  15

Lys Asp Asn Asn Arg Glu Glu Met Tyr Ile Arg Tyr Leu Tyr Lys Leu
            20                  25                  30

Arg Asp Leu His Leu Asp Cys Asp Asn Tyr Thr Glu Ala Ala Tyr Thr
        35                  40                  45

Leu Leu Leu His Thr Trp Leu Leu Lys Trp Ser Asp Glu Gln Cys Ala
    50                  55                  60

Ser Gln Val Met Gln Thr Gly Gln Gln His Pro Gln Thr His Arg Gln
65                  70                  75                  80

Leu Lys Glu Thr Leu Tyr Glu Thr Ile Ile Gly Tyr Phe Asp Lys Gly
                85                  90                  95

Lys Met Trp Glu Glu Ala Ile Ser Leu Cys Lys Glu Leu Ala Glu Gln
            100                 105                 110

Tyr Glu Met Glu Ile Phe Asp Tyr Glu Leu Leu Ser Gln Asn Leu Ile
        115                 120                 125

Gln Gln Ala Lys Phe Tyr Glu Ser Ile Met Lys Ile Leu Arg Pro Lys
    130                 135                 140

Pro Asp Tyr Phe Ala Val Gly Tyr Tyr Gln Gly Phe Pro Ser Phe
145                 150                 155                 160

Leu Arg Asn Lys Val Phe Ile Tyr Arg Gly Lys Glu Tyr Glu Arg Arg
                165                 170                 175

Glu Asp Phe Gln Met Gln Leu Met Thr Gln Phe Pro Asn Ala Glu Lys
            180                 185                 190

Met Asn Thr Thr Ser Ala Pro Gly Asp Asp Val Lys Asn Ala Pro Gly
        195                 200                 205

Gln Tyr Ile Gln Cys Phe Thr Val Gln Pro Val Leu Asp Glu His Pro
    210                 215                 220

Arg Phe Lys Asn Lys Pro Val Pro Asp Gln Ile Ile Asn Phe Tyr Lys
225                 230                 235                 240

Ser Asn Tyr Val Gln Arg Phe His Tyr Ser Arg Pro Val Arg Arg Gly
                245                 250                 255

Thr Val Asp Pro Glu Asn Glu Phe Ala Ser Met Trp Ile Glu Arg Thr
            260                 265                 270

Ser Phe Val Thr Ala Tyr Lys Leu Pro Gly Ile Leu Arg Trp Phe Glu
        275                 280                 285

Val Val His Met Ser Gln Thr Thr Ile Ser Pro Leu Glu Asn Ala Ile
    290                 295                 300

Glu Thr Met Ser Thr Ala Asn Glu Lys Ile Leu Met Met Ile Asn Gln
305                 310                 315                 320

Tyr Gln Ser Asp Glu Thr Leu Pro Ile Asn Pro Leu Ser Met Leu Leu
                325                 330                 335

Asn Gly Ile Val Asp Pro Ala Val Met Gly Gly Phe Ala Lys Tyr Glu
            340                 345                 350
```

Lys Ala Phe Thr Glu Glu Tyr Val Arg Asp His Pro Glu Asp Gln
                355                 360                 365

Asp Lys Leu Thr His Leu Lys Asp Leu Ile Ala Trp Gln Ile Pro Phe
    370                 375                 380

Leu Gly Ala Gly Ile Lys Ile His Glu Lys Arg Val Ser Asp Asn Leu
385                 390                 395                 400

Arg Pro Phe His Asp Arg Met Glu Glu Cys Phe Lys Asn Leu Lys Met
                405                 410                 415

Lys Val Glu Lys Glu Tyr Gly Val Arg Glu Met
                420                 425

<210> SEQ ID NO 2
<211> LENGTH: 365
<212> TYPE: PRT
<213> ORGANISM: Homo sapiens

<400> SEQUENCE: 2

Met Asp Gly Pro Ala Glu Pro Gln Ile Pro Gly Leu Trp Asp Thr Tyr
1               5                   10                  15

Glu Asp Asp Ile Ser Glu Ile Ser Gln Lys Leu Pro Gly Glu Tyr Phe
                20                  25                  30

Arg Tyr Lys Gly Val Pro Phe Pro Val Gly Leu Tyr Ser Leu Glu Ser
            35                  40                  45

Ile Ser Leu Ala Glu Asn Thr Gln Asp Val Arg Asp Asp Ile Phe
        50                  55                  60

Ile Ile Thr Tyr Pro Lys Ser Gly Thr Thr Trp Met Ile Glu Ile Ile
65                  70                  75                  80

Cys Leu Ile Leu Lys Glu Gly Asp Pro Ser Trp Ile Arg Ser Val Pro
                85                  90                  95

Ile Trp Glu Arg Ala Pro Trp Cys Glu Thr Ile Val Gly Ala Phe Ser
                100                 105                 110

Leu Pro Asp Gln Tyr Ser Pro Arg Leu Met Ser Ser His Leu Pro Ile
                115                 120                 125

Gln Ile Phe Thr Lys Ala Phe Phe Ser Ser Lys Ala Lys Val Ile Tyr
                130                 135                 140

Met Gly Arg Asn Pro Arg Asp Val Val Val Ser Leu Tyr His Tyr Ser
145                 150                 155                 160

Lys Ile Ala Gly Gln Leu Lys Asp Pro Gly Thr Pro Asp Gln Phe Leu
                165                 170                 175

Arg Asp Phe Leu Lys Gly Glu Val Gln Phe Gly Ser Trp Phe Asp His
                180                 185                 190

Ile Lys Gly Trp Leu Arg Met Lys Gly Lys Asp Asn Phe Leu Phe Ile
            195                 200                 205

Thr Tyr Glu Glu Leu Gln Gln Asp Leu Gln Gly Ser Val Glu Arg Ile
                210                 215                 220

Cys Gly Phe Leu Gly Arg Pro Leu Gly Lys Glu Ala Leu Gly Ser Val
225                 230                 235                 240

Val Ala His Ser Thr Phe Ser Ala Met Lys Ala Asn Thr Met Ser Asn
                245                 250                 255

Tyr Thr Leu Leu Pro Pro Ser Leu Asp His Arg Arg Gly Ala Phe
                260                 265                 270

Leu Arg Lys Gly Val Cys Gly Asp Trp Lys Asn His Phe Thr Val Ala
            275                 280                 285

Gln Ser Glu Ala Phe Asp Arg Ala Tyr Arg Lys Gln Met Arg Gly Met
                290                 295                 300

Pro Thr Phe Pro Trp Asp Glu Asp Pro Glu Asp Gly Ser Pro Asp
305                 310                 315                 320

Pro Glu Pro Ser Pro Glu Pro Glu Pro Lys Pro Ser Leu Glu Pro Asn
                325                 330                 335

Thr Ser Leu Glu Arg Glu Pro Arg Pro Asn Ser Ser Pro Ser Pro Ser
            340                 345                 350

Pro Gly Gln Ala Ser Glu Thr Pro His Pro Arg Pro Ser
        355                 360                 365

<210> SEQ ID NO 3
<211> LENGTH: 624
<212> TYPE: PRT
<213> ORGANISM: Homo sapiens

<400> SEQUENCE: 3

Met Pro Arg Pro Arg Pro Leu Leu Leu Ala Val Met Ala Ala Thr Leu
1               5                   10                  15

Ala Asp Ile Ile Leu Ala Ala Asp Pro Ala Pro Ala Gly Pro Ala Pro
            20                  25                  30

Arg Pro Pro Asn Phe Leu Leu Ile Met Ala Asp Asp Leu Gly Ile Gly
        35                  40                  45

Asp Leu Gly Cys Tyr Gly Asn Lys Thr Leu Arg Thr Pro His Leu Asp
    50                  55                  60

Arg Leu Ala Arg Glu Gly Val Lys Leu Thr Gln His Leu Ala Ala Ala
65                  70                  75                  80

Pro Leu Cys Thr Pro Ser Arg Ala Ala Phe Leu Thr Gly Arg Tyr Pro
                85                  90                  95

Pro Arg Ser Gly Met Ala Ala His Gly Arg Val Gly Val Tyr Leu Phe
            100                 105                 110

Thr Ala Ser Ser Gly Gly Leu Pro Pro Ser Glu Val Thr Met Ala Arg
        115                 120                 125

Leu Leu Lys Gly Arg Gly Tyr Ala Thr Ala Leu Ile Gly Lys Trp His
    130                 135                 140

Leu Gly Leu Ser Cys Arg Gly Ala Thr Asp Phe Cys His His Pro Leu
145                 150                 155                 160

Arg His Gly Phe Asp Arg Phe Leu Gly Val Pro Thr Thr Asn Leu Arg
                165                 170                 175

Asp Cys Arg Pro Gly Ala Gly Thr Val Phe Gly Pro Ala Leu Arg Val
            180                 185                 190

Phe Ala Ala Gly Pro Leu Ala Ala Leu Gly Ala Ser Leu Ala Ala Met
        195                 200                 205

Ala Ala Ala Arg Trp Ala Gly Leu Ala Arg Val Pro Gly Trp Ala Leu
    210                 215                 220

Ala Gly Thr Ala Ala Ala Met Leu Ala Val Gly Gly Pro Arg Ser Ala
225                 230                 235                 240

Ser Cys Leu Gly Phe Arg Pro Ala Asn Cys Phe Leu Met Asp Asp Leu
                245                 250                 255

Ala Val Ala Gln Arg Pro Thr Asp Tyr Gly Gly Leu Thr Arg Arg Leu
            260                 265                 270

Ala Asp Glu Ala Ala Leu Phe Leu Arg Arg Asn Arg Ala Arg Pro Phe
        275                 280                 285

Leu Leu Phe Leu Ser Phe Leu His Val His Thr Ala His Phe Ala Asp
    290                 295                 300

Pro Gly Phe Ala Gly Arg Ser Leu His Gly Ala Tyr Gly Asp Ser Val

```
            305                 310                 315                 320

Glu Glu Met Asp Trp Gly Val Gly Arg Val Leu Ala Ala Leu Asp Glu
                        325                 330                 335

Leu Gly Leu Ala Arg Glu Thr Leu Val Tyr Phe Thr Ser Asp His Gly
                        340                 345                 350

Ala His Val Glu Glu Leu Gly Pro Arg Gly Glu Arg Met Gly Gly Ser
                        355                 360                 365

Asn Gly Val Phe Arg Gly Gly Lys Gly Asn Asn Trp Glu Gly Gly Val
                    370                 375                 380

Arg Val Pro Cys Leu Val Arg Trp Pro Arg Glu Leu Ser Pro Gly Arg
        385                 390                 395                 400

Val Val Ala Glu Pro Thr Ser Leu Met Asp Val Phe Pro Thr Val Ala
                        405                 410                 415

Arg Leu Ala Gly Ala Glu Leu Pro Gly Asp Arg Val Ile Asp Gly Arg
                        420                 425                 430

Asp Leu Met Pro Leu Leu Arg Gly Asp Ala Gln Arg Ser Glu His Glu
                        435                 440                 445

Phe Leu Phe His Tyr Cys Asn Ala Tyr Leu Gln Ala Val Arg Trp His
                    450                 455                 460

Asn Gly Ser Ala Val Trp Lys Ala Phe Tyr Phe Thr Pro Asn Phe Ala
        465                 470                 475                 480

Pro Ala Gly Ala Asn Gly Cys Phe Ser Thr His Val Cys Leu Cys Ala
                        485                 490                 495

Gly Pro Ala His Val Thr Ala His Asp Pro Pro Leu Leu Phe Asp Leu
                        500                 505                 510

Thr Arg Asp Pro Gly Glu Arg Pro Leu Thr Pro Glu Ala Glu Pro
                        515                 520                 525

Arg His Arg Glu Val Leu Asp Ala Ile Asp Ala Ala Arg Ala His
                    530                 535                 540

Arg Ala Arg Leu Arg Pro Ala Pro Asp Gln Leu Ala Pro Arg His Leu
        545                 550                 555                 560

Met Trp Lys Pro Trp Leu Gln Leu Trp Gly Gly Gly Ala Gly Gly
                        565                 570                 575

Gly Ala Gly Ala Gln Asp Asp Ser Gly His Ala His Gly Asp Gly Ser
                        580                 585                 590

His Ala His Asp Asp Pro Gly His Ala Gln Asp Arg Gly Asp Asp
                    595                 600                 605

Ala His Tyr Gly Gly His Ala Thr Thr Arg Thr Gln Ala Thr Pro Arg
        610                 615                 620

<210> SEQ ID NO 4
<211> LENGTH: 19
<212> TYPE: DNA
<213> ORGANISM: Homo sapiens
<220> FEATURE:
<221> NAME/KEY: misc_feature
<223> OTHER INFORMATION: siRNA sense strand against human SULT2B1b

<400> SEQUENCE: 4
ccauccagau cuucaccaa                                                   19

<210> SEQ ID NO 5
<211> LENGTH: 19
<212> TYPE: DNA
<213> ORGANISM: Homo sapiens
<220> FEATURE:
<221> NAME/KEY: misc_feature
```

<223> OTHER INFORMATION: siRNA sense strand against human SULT2B1b

<400> SEQUENCE: 5
cccucuauca uuacuccaa                                                    19

<210> SEQ ID NO 6
<211> LENGTH: 19
<212> TYPE: DNA
<213> ORGANISM: Homo sapiens
<220> FEATURE:
<221> NAME/KEY: misc_feature
<223> OTHER INFORMATION: siRNA sense strand against human SULT2B1b

<400> SEQUENCE: 6
ccacauuaag ggcuggcuu                                                    19

<210> SEQ ID NO 7
<211> LENGTH: 19
<212> TYPE: DNA
<213> ORGANISM: Homo sapiens
<220> FEATURE:
<221> NAME/KEY: misc_feature
<223> OTHER INFORMATION: siRNA sense strand against human SULT2B1b

<400> SEQUENCE: 7
gcgacuggaa gaaccacuu                                                    19

<210> SEQ ID NO 8
<211> LENGTH: 50
<212> TYPE: DNA
<213> ORGANISM: Homo sapiens
<220> FEATURE:
<221> NAME/KEY: misc_feature
<223> OTHER INFORMATION: shRNA against human SULT2B1b

<400> SEQUENCE: 8
caccggugaa uacuuccggu acaagcgaac uuguaccgga aguauucacc                  50

<210> SEQ ID NO 9
<211> LENGTH: 50
<212> TYPE: DNA
<213> ORGANISM: Homo sapiens
<220> FEATURE:
<221> NAME/KEY: misc_feature
<223> OTHER INFORMATION: shRNA against human SULT2B1b

<400> SEQUENCE: 9
caccgcggga cgacgacauc uuuaucgaaa uaaagauguc gucguccgc                   50

<210> SEQ ID NO 10
<211> LENGTH: 50
<212> TYPE: DNA
<213> ORGANISM: Homo sapiens
<220> FEATURE:
<221> NAME/KEY: misc_feature
<223> OTHER INFORMATION: shRNA against human SULT2B1b

<400> SEQUENCE: 10
caccgcuucg gaugaagggc aaagacgaau cuuugcccuu cauccgaagc                  50

<210> SEQ ID NO 11
<211> LENGTH: 19
<212> TYPE: DNA
<213> ORGANISM: Homo sapiens
<220> FEATURE:
<221> NAME/KEY: misc_feature
<223> OTHER INFORMATION: siRNA sense strand against human STS

<400> SEQUENCE: 11
ggaaauggca ccuugggau                                                19

<210> SEQ ID NO 12
<211> LENGTH: 19
<212> TYPE: DNA
<213> ORGANISM: Homo sapiens
<220> FEATURE:
<221> NAME/KEY: misc_feature
<223> OTHER INFORMATION: siRNA sense strand against human STS

<400> SEQUENCE: 12
gcuucaagag gcuggucuu                                                19

<210> SEQ ID NO 13
<211> LENGTH: 19
<212> TYPE: DNA
<213> ORGANISM: Homo sapiens
<220> FEATURE:
<221> NAME/KEY: misc_feature
<223> OTHER INFORMATION: siRNA sense strand against human STS

<400> SEQUENCE: 13
gggagcacau guagaagaa                                                19

<210> SEQ ID NO 14
<211> LENGTH: 19
<212> TYPE: DNA
<213> ORGANISM: Homo sapiens
<220> FEATURE:
<221> NAME/KEY: misc_feature
<223> OTHER INFORMATION: siRNA sense strand against human STS

<400> SEQUENCE: 14
ggagaaauuc auggcggaa                                                19

<210> SEQ ID NO 15
<211> LENGTH: 50
<212> TYPE: DNA
<213> ORGANISM: Homo sapiens
<220> FEATURE:
<221> NAME/KEY: misc_feature
<223> OTHER INFORMATION: shRNA against human STS

<400> SEQUENCE: 15
caccggauga gcugucacag caagacgaau cuugcuguga cagcucaucc              50

<210> SEQ ID NO 16
<211> LENGTH: 50
<212> TYPE: DNA
<213> ORGANISM: Homo sapiens
<220> FEATURE:
<221> NAME/KEY: misc_feature
<223> OTHER INFORMATION: shRNA against human STS

<400> SEQUENCE: 16
caccgggagc acauguagaa gaagucgaaa cuucuucuac augugcuccc              50

<210> SEQ ID NO 17
<211> LENGTH: 50
<212> TYPE: DNA
<213> ORGANISM: Homo sapiens
<220> FEATURE:
<221> NAME/KEY: misc_feature
<223> OTHER INFORMATION: shRNA against human STS -continued

```
<400> SEQUENCE: 17
caccggugca ggagguaccu uaacucgaaa guuaagguac cuccugcacc                    50
```

IMMUNOREGULATORY AGENT

This application is a Divisional of application Ser. No. 15/775,895, filed May 14, 2018, which is a National Stage of International Application No. PCT/JP2016/084259, filed Nov. 18, 2016, which claims priority to Japanese Application No. 2015-228190, filed Nov. 20, 2015. The entire contents of the prior applications are hereby incorporated by reference herein in their entirety.

The present application contains a Sequence Listing that has been submitted electronically in ASCII format and is hereby incorporated by reference in its entirety. The ASCII copy, created on May 14, 2018, is named SequenceListing.txt and is 15,880 bytes in size.

TECHNICAL FIELD

The present invention relates to a novel immunoregulatory methodology, an immunoregulatory agent manufactured based on the methodology, and use of the immunoregulatory agent. More specifically, the present invention relates to a methodology for immunosuppression, the formation of an immune-privileged site, and the cancellation of the formation of an immune-privileged site, based on the inhibitory function of cholesterol 3-sulfate for Dedicator of cytokinesis 2 (DOCK2), an immunoregulatory agent manufactured based on the methodology, and use of the immunoregulatory agent.

BACKGROUND ART

It has long been known that the inflammation mediated by immune cells or allogeneic graft rejection is markedly suppressed in specific organs such as the eye, the brain, and the pregnant mother's uterus, and this phenomenon is called immune privilege (for example, see NPL 1). Furthermore, there is a report indicating that cancer tissues have such immune privilege (for example, see NPL 2). However, the substance of the immune privilege is unclear.

CITATION LIST

Non-Patent Literature

[NPL 1] Niederkorn J. Y, See no evil, hear no evil, do no evil: the lessons of immune privilege, Nat Immunol., 7(4), 354-359, 2006.

[NPL 2] Joyce J. A. and Fearon D. T., T cell exclusion, immune privilege, and the tumor microenvironment, Science, 348(6230), 74-80, 2015.

SUMMARY OF INVENTION

Technical Problem

Antibody therapy in which an immune checkpoint molecule is targeted has become one of the most hopeful cancer treatments at present. However, in order for the antibody therapy to effectively act, the immune evasion mechanism (immune privilege) of cancer needs to be canceled.

Furthermore, when the substance of the immune privilege is clarified such that the immune privilege can be artificially granted to cells or tissues, a medical technology will be developed through which transplantable allogeneic tissues can be prepared for transplantation or regenerative medicine.

Therefore, an object of the present invention is to clarify the substance of the immune privilege and to provide a novel immunoregulatory agent. More specifically, an object of the present invention is to provide a medical technology for preparing an agent for treating inflammatory diseases, a pharmaceutical product for stimulating cancer immunity, and an immune-privileged tissue which can be used for allogeneic transplantation.

Solution to Problem

The present invention includes the following aspects.

[1] An immunoregulatory agent containing a regulatory agent that regulates Dedicator of cytokinesis 2 (DOCK2)-mediated Rac activation as an active ingredient.

[2] The immunoregulatory agent described in [1], in which the regulatory agent to regulate DOCK2-mediated Rac activation is a compound represented by Formula (1), a pharmacologically accepted salt thereof, or a solvate of these.

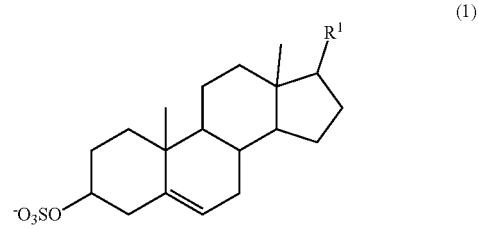

(1)

[In Formula (1), $R^1$ represents an alkyl group having 3 to 12 carbon atoms that may be linear, branched, or cyclic and may be substituted or represents an aromatic group having 6 to 12 carbon atoms that may be substituted.]

[3] The immunoregulatory agent described in [1], in which the regulatory agent to regulate DOCK2-mediated Rac activation is a specific substance that binds to cholesterol 3-sulfate or a salt thereof.

[4] The immunoregulatory agent described in [3], in which the specific binding substance is a protein which has an amino acid sequence described in SEQ ID NO: 1 or a protein which has an amino acid sequence formed by deletion, substitution, or addition of one or several amino acids in the amino acid sequence described in SEQ ID NO: 1 and exhibits binding activity for cholesterol 3-sulfate or a salt thereof.

[5] The immunoregulatory agent described in [1], in which the regulatory agent to regulate DOCK2-mediated Rac activation is an expression vector of a protein which has an amino acid sequence described in SEQ ID NO: 1 or an expression vector of a protein which has an amino acid sequence formed by deletion, substitution, or addition of one or several amino acids in the amino acid sequence described in SEQ ID NO: 1 and exhibits binding activity for cholesterol 3-sulfate or a salt thereof.

[6] The immunoregulatory agent described in [1], in which the regulatory agent to regulate DOCK2-mediated Rac activation is a protein which has an amino acid sequence described in SEQ ID NO: 2; a protein which has an amino acid sequence formed by deletion, substitution, or addition of one or several amino acids in the amino acid sequence described in SEQ ID NO: 2 and has an activity to add a sulfonic acid group to the hydroxyl group at position 3 of cholesterol; an expression vector of the protein which has the amino acid sequence described in SEQ ID NO: 2; an expression vector of the protein which has an amino acid sequence formed by deletion, substitution, or addition of one or several amino acids in the amino acid sequence described in SEQ ID NO: 2 and has an activity to add a sulfonic acid group to the hydroxyl group at position 3 of cholesterol; siRNA, shRNA, miRNA, ribozyme, or an antisense nucleic acid inhibiting the expression of the protein which has the amino acid sequence described in SEQ ID NO: 2; or an inhibitor of the protein which has the amino acid sequence described in SEQ ID NO: 2.

[7] The immunoregulatory agent described in [1], in which the regulatory agent to regurate DOCK2-mediated Rac activation is a protein which has an amino acid sequence described in SEQ ID NO: 3; a protein which has an amino acid sequence formed by deletion, substitution, or addition of one or several amino acids in an amino acid sequence described in SEQ ID NO: 3 and acts to remove a sulfonic acid group of cholesterol 3-sulfate; an expression vector of the protein which has the amino acid sequence described in SEQ ID NO: 3; an expression vector of the protein which has the amino acid sequence formed by deletion, substitution, or addition of one or several amino acids in the amino acid sequence described in SEQ ID NO: 3 and acts to remove a sulfonic acid group of cholesterol 3-sulfate; siRNA, shRNA, miRNA, ribozyme, or an antisense nucleic acid inhibiting the expression of the protein which has the amino acid sequence described in SEQ ID NO: 3; or an inhibitor of the protein which has the amino acid sequence described in SEQ ID NO: 3.

Advantageous Effects of Invention

According to the present invention, a novel immunoregulatory agent can be provided.

Figure 3:
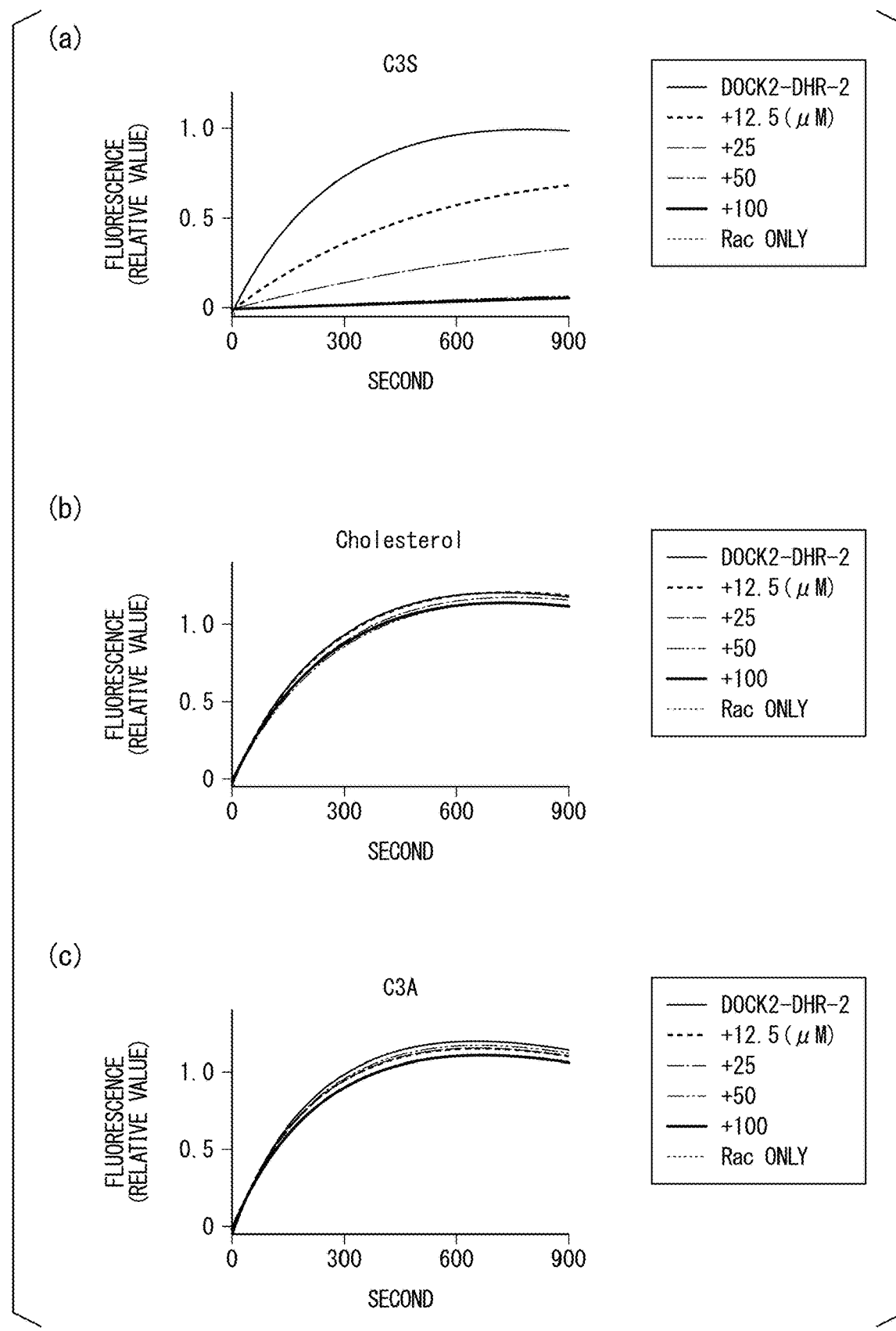

(a) to (c) of FIG. 3 are graphs showing the results of Experimental Example 2.

Figure 4:
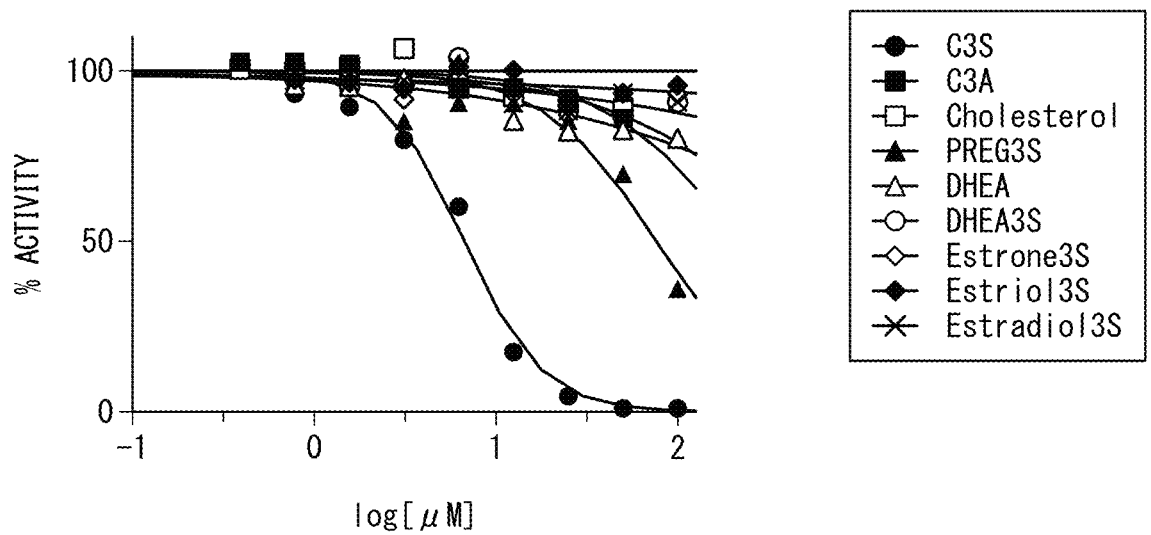

FIG. 4 is a graph showing the results obtained by measuring the Rac activation in Experimental Example 2 in the presence of various steroid compounds at various concentrations.

Figure 5:
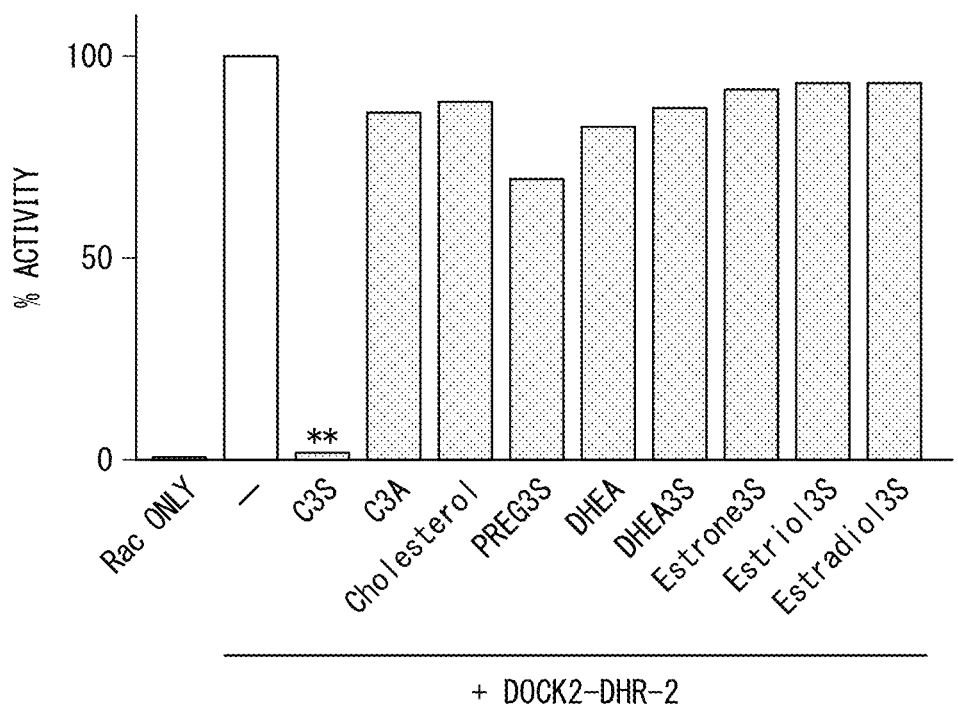

FIG. 5 is a graph showing the results obtained by comparing the Rac activation in Experimental Example 2 in the presence of various 50 μM steroid compounds.

Figure 6:
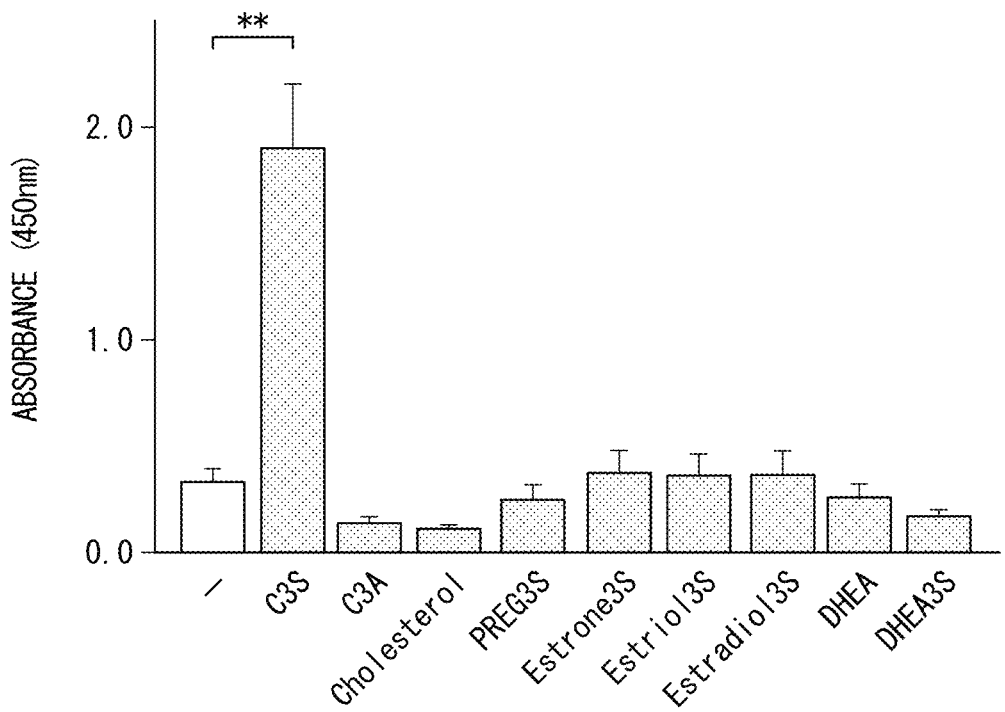

FIG. 6 is a graph showing the results of Experimental Example 3.

Figure 7:
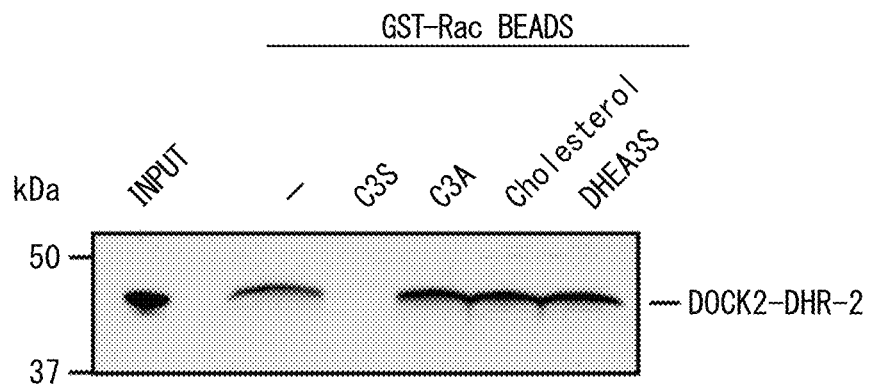

FIG. 7 is a photograph showing the results obtained by detecting DOCK2-DHR-2 bond to GST-Rac beads by a Western blotting method in Experimental Example 4.

Figure 8:
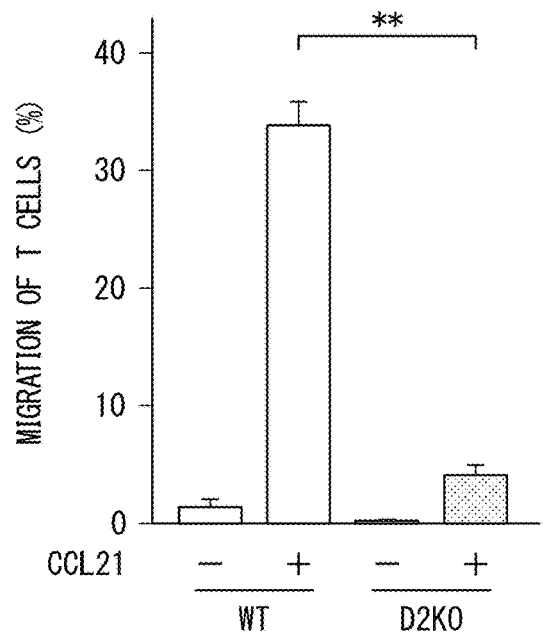

FIG. 8 is a graph showing the results obtained by comparing T cells derived from a wild-type mice and a DOCK2-deficient mice in terms of their ability to migrate to CCL21 in Experimental Example 5.

Figure 9:
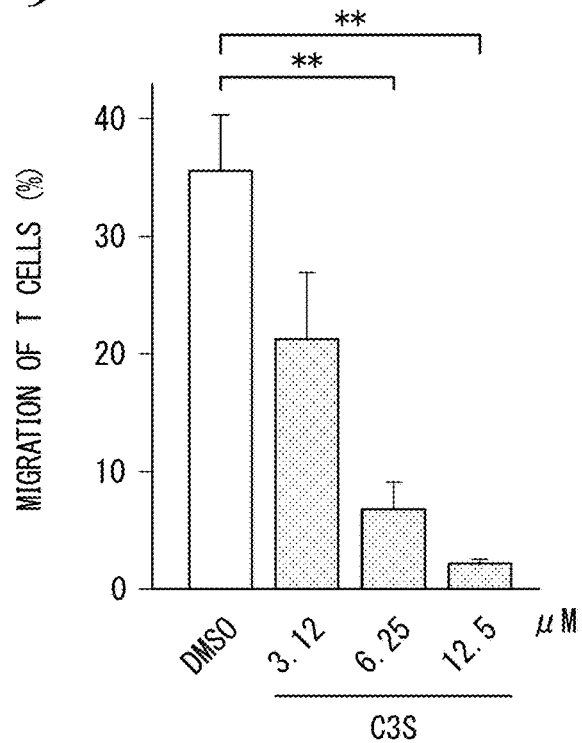

FIG. 9 is a graph showing the results obtained by examining the inhibitory effect of cholesterol 3-sulfate on the T cell migration in Experimental Example 5.

Figure 10:
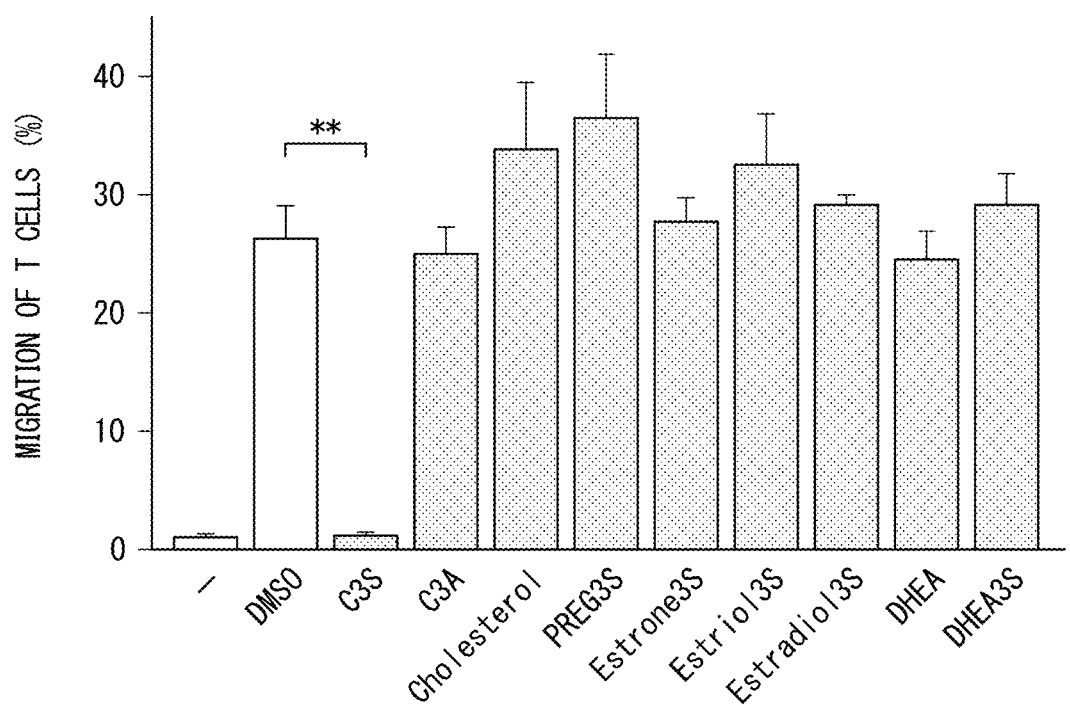

FIG. 10 is a graph showing the results obtained by examining the effects of various steroid compounds on the lymphocyte migration in Experimental Example 6.

Figure 11:
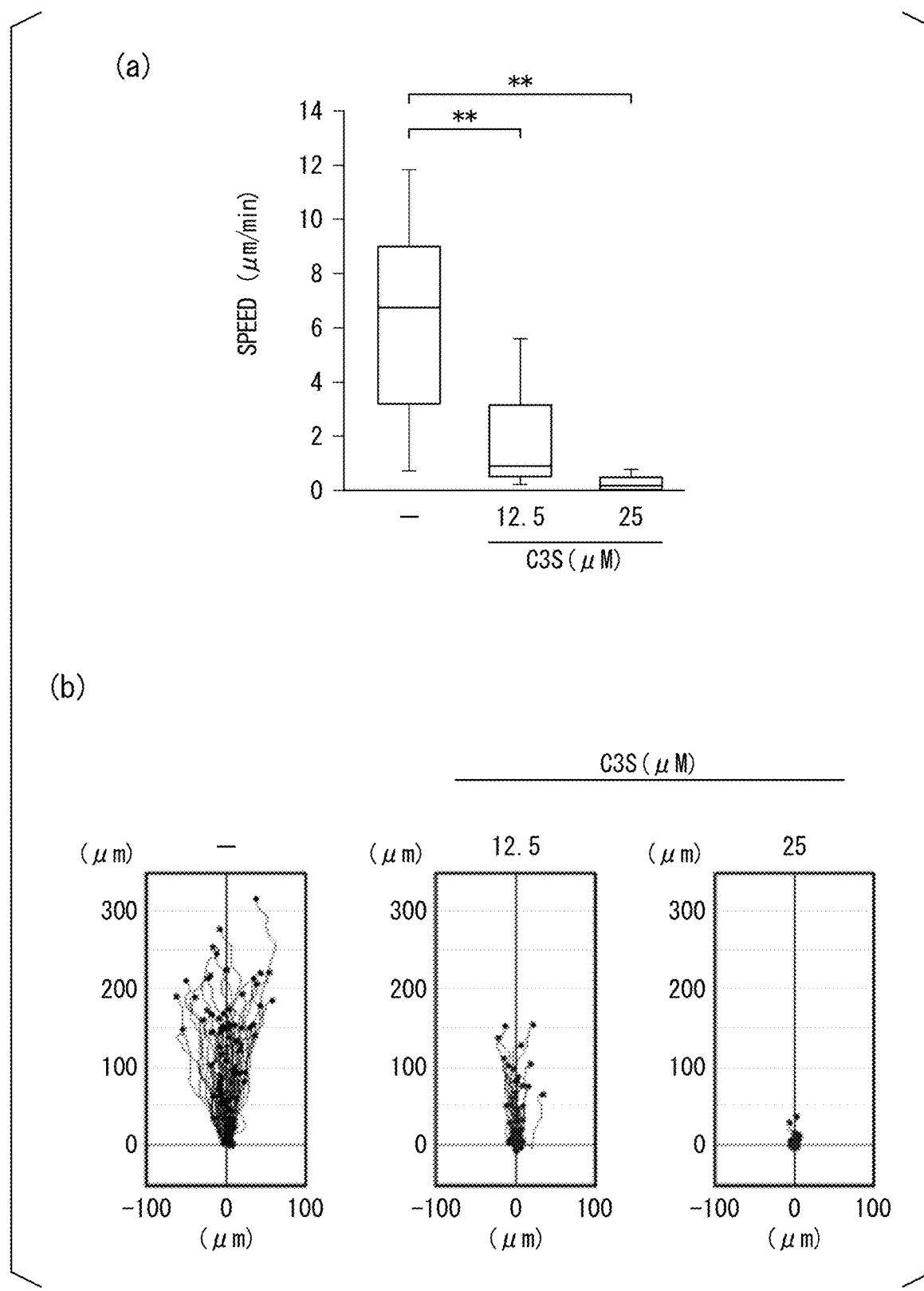

(a) and (b) of FIG. 11 are graphs showing the results obtained by examining the effect of cholesterol 3-sulfate on neutrophil chemotaxis in response to fMLP in Experimental Example 7.

Figure 12:
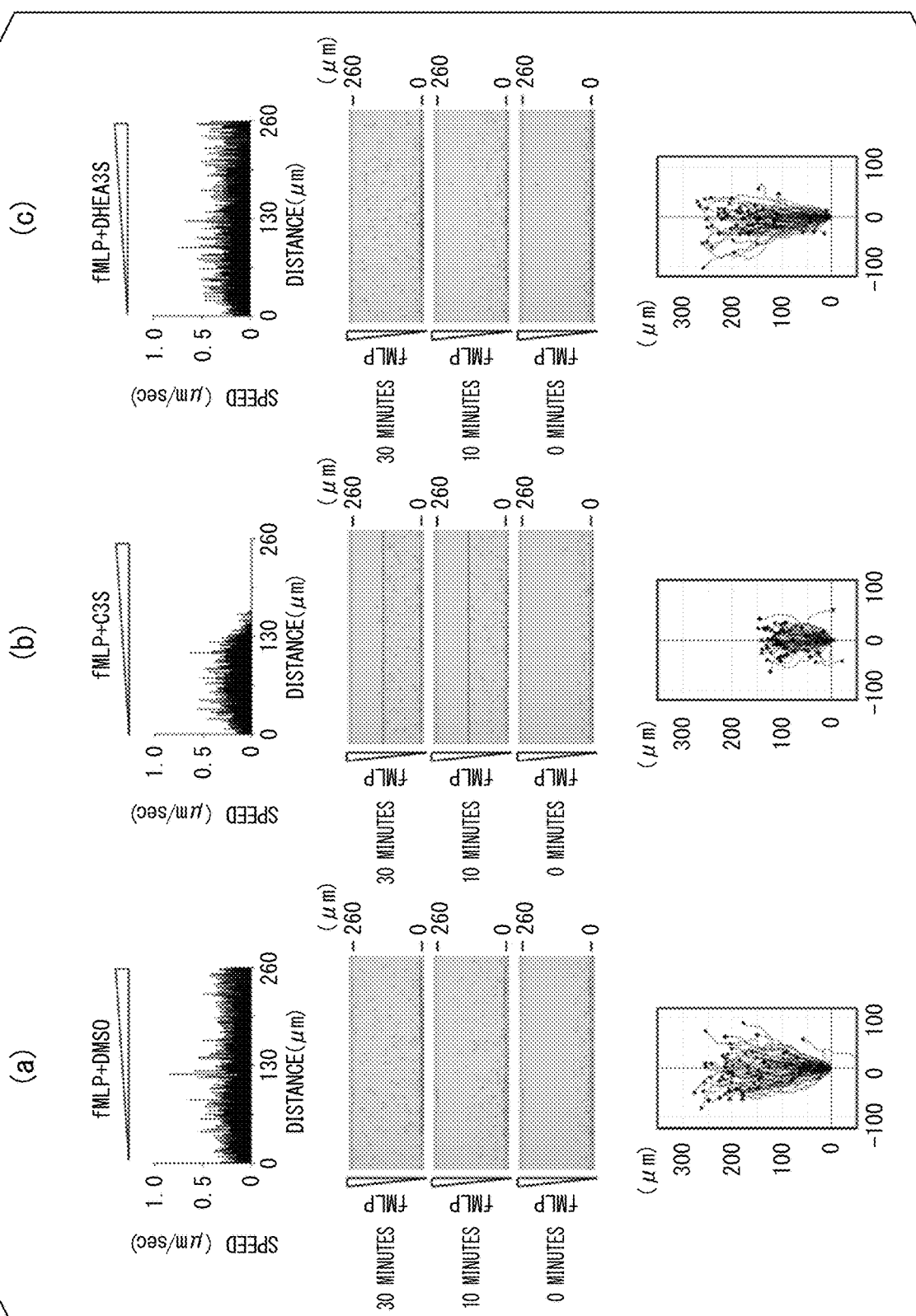

(a) to (c) of FIG. 12 are graphs and photographs showing the results of Experimental Example 8.

Figure 13:
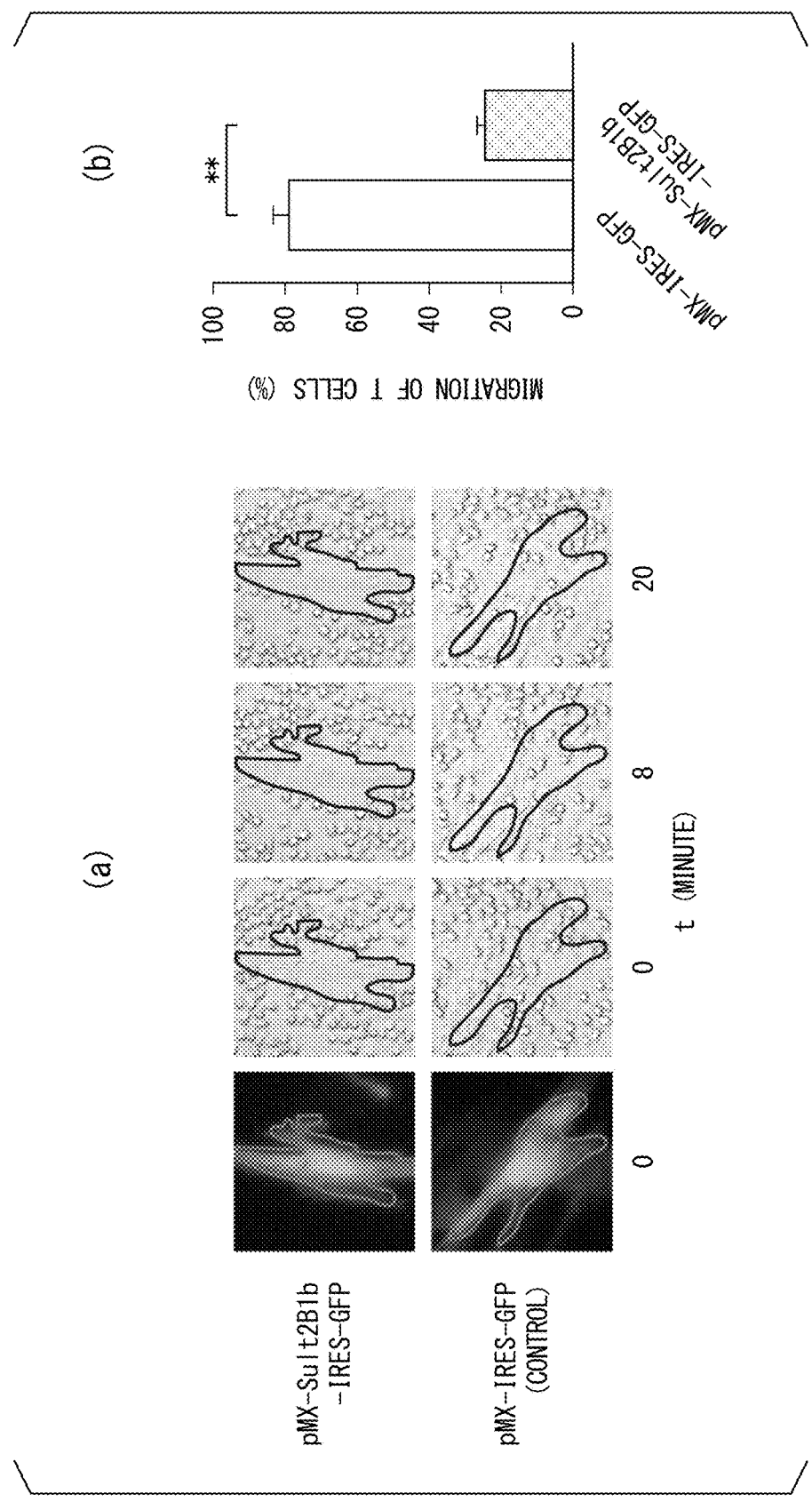

(a) of FIG. 13 shows time-lapse images showing the migratory properties of T cells on stroma cells expressing GFP alone as a control or those expressing Sult2B1b gene and GFP in Experimental Example 9, and (b) of FIG. 13 is a graph showing the results obtained by comparing the migratory properties of T cells on stroma cells expressing GFP alone as a control or those expressing the Sult2B1b gene and GFP in Experimental Example 9.

Figure 14:
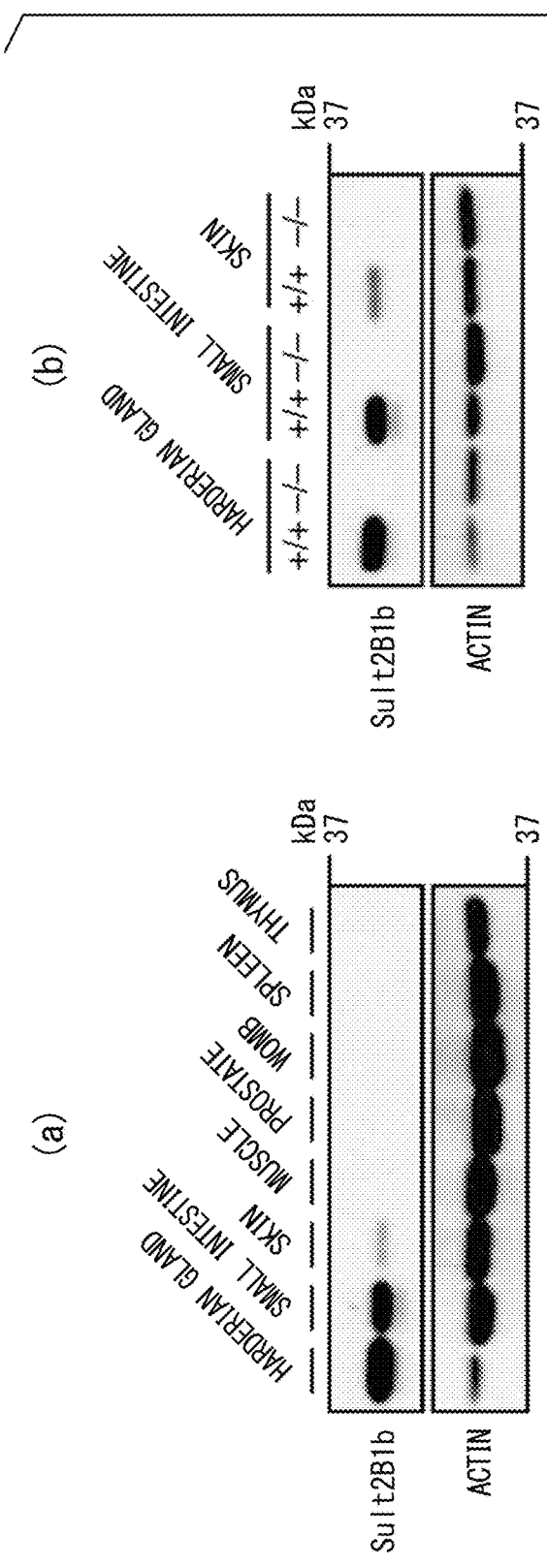

(a) of FIG. 14 is photographs showing the results obtained by detecting an Sult2B1b protein by a Western blotting method in Experimental Example 10, and (b) of FIG. 14 shows photographs showing the results obtained by detecting the expression of the Sult2B1b protein in each tissue from a wild-type mouse (+/+) and an Sult2B1b gene knockout mouse (−/−).

Figure 15:
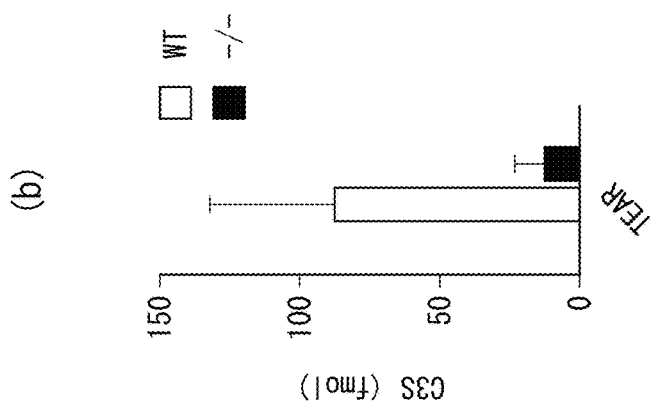
Figure 15:
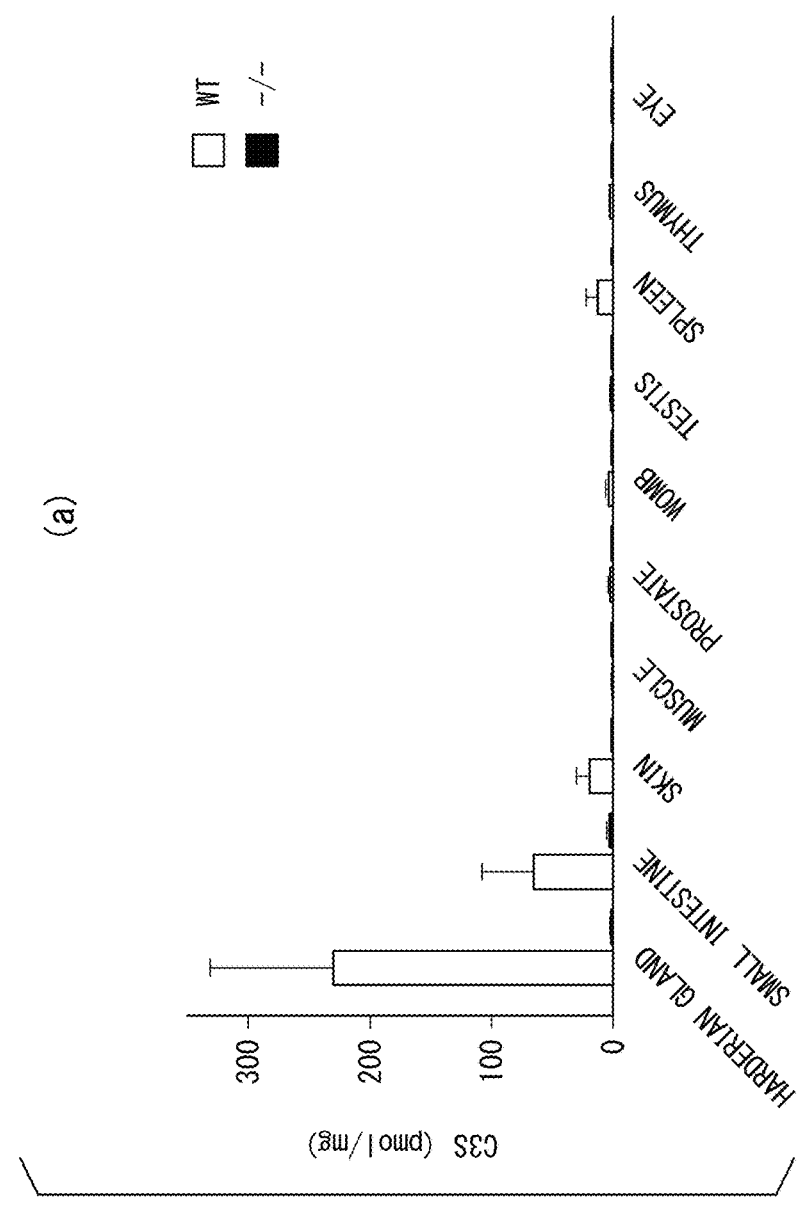

(a) and (b) of FIG. 15 are graphs showing the results obtained by quantifying cholesterol 3-sulfate in Experimental Example 11.

Figure 16:
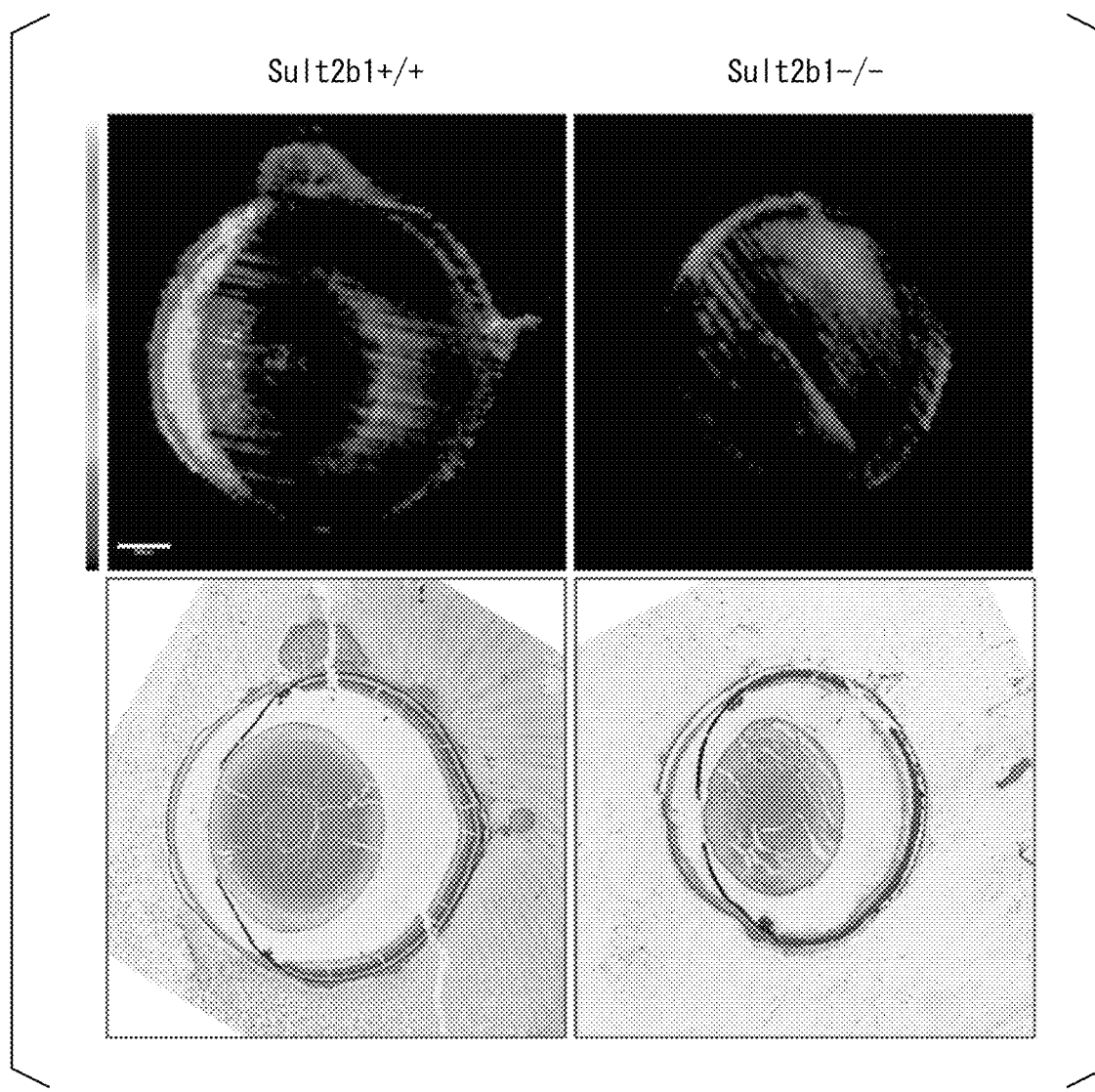

FIG. 16 shows the micrograph obtained by mass spectrometry imaging for localization of cholesterol 3-sulfate in eyeballs of mice in Experimental Example 11.

Figure 17:
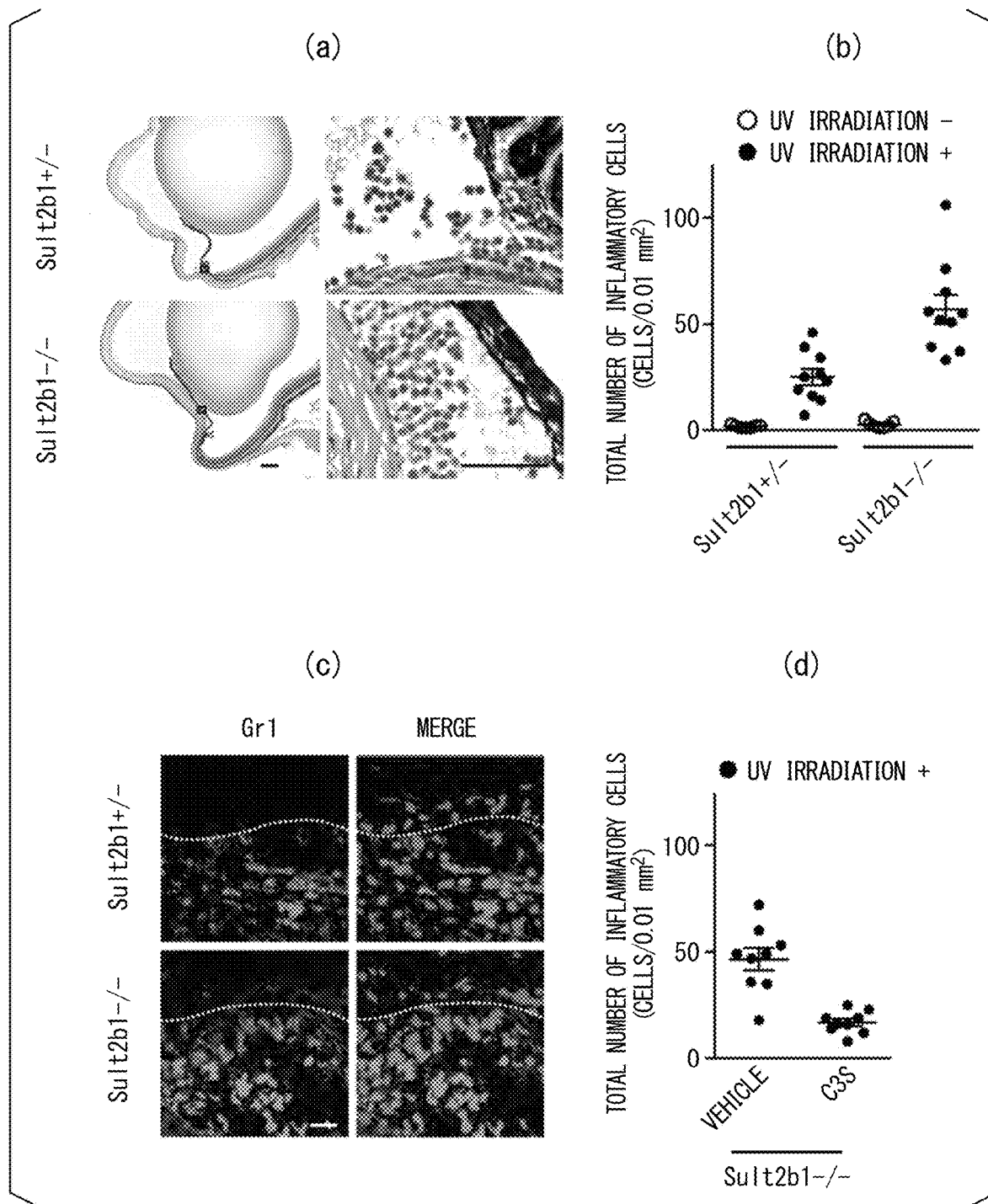

(a) of FIG. 17 shows the micrographs of eyeball sections of mice in Experimental Example 12. (b) and (d) of FIG. 17 are graphs showing the results obtained by measuring the total number of inflammatory cells infiltrating into the anterior chamber of eye of the mice in Experimental Example 12. (c) of FIG. 17 shows fluorescence micrographs showing the results on immunostaining of the eyeball sections of the mice using an antibody against Gr1, a marker for neutrophils in Experimental Example 12.

Figure 18:
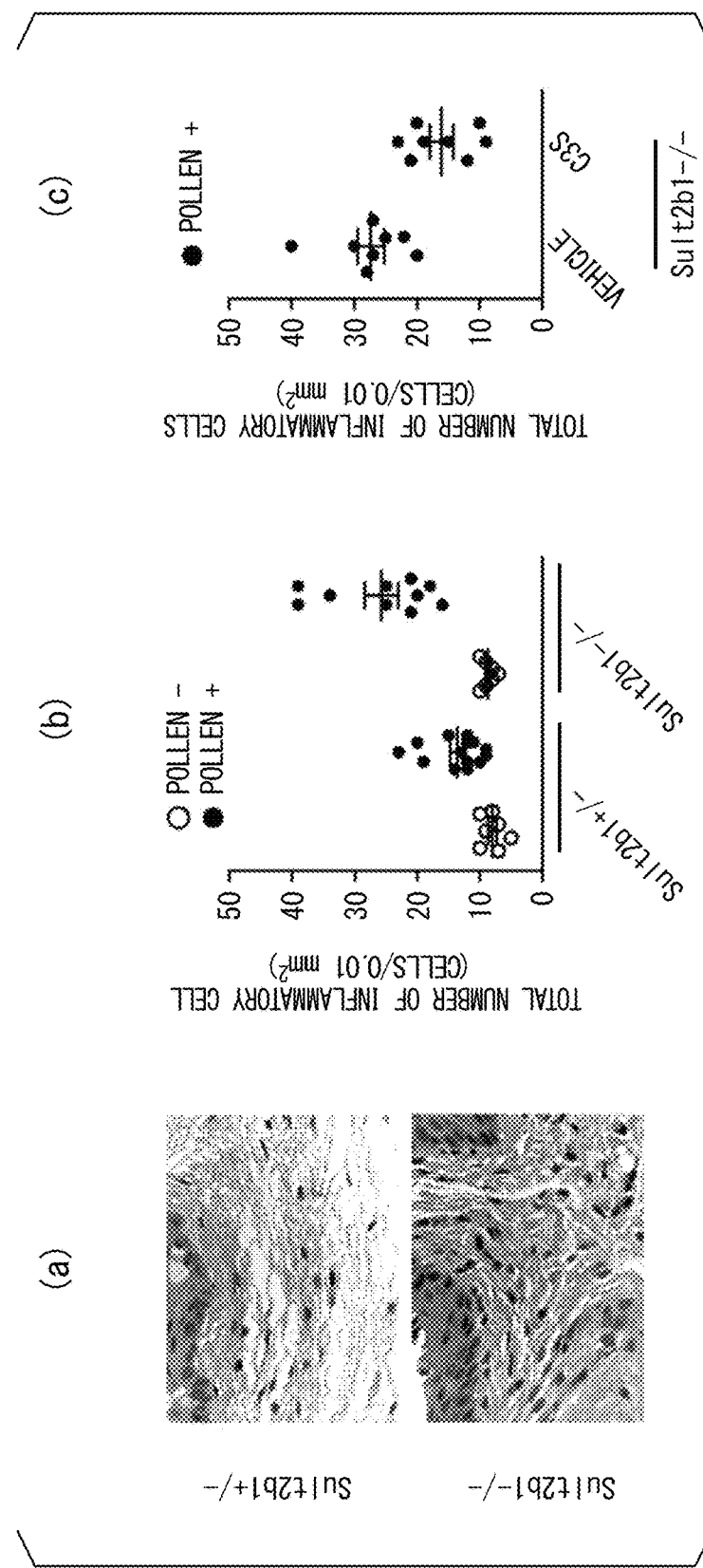

(a) of FIG. 18 shows the micrographs of eyeball sections of mice in Experimental Example 13. (b) and (c) of FIG. 18 are graphs showing the results obtained by measuring the total number of inflammatory cells infiltrating into the conjunctiva of the mice in Experimental Example 13.

Figure 19:
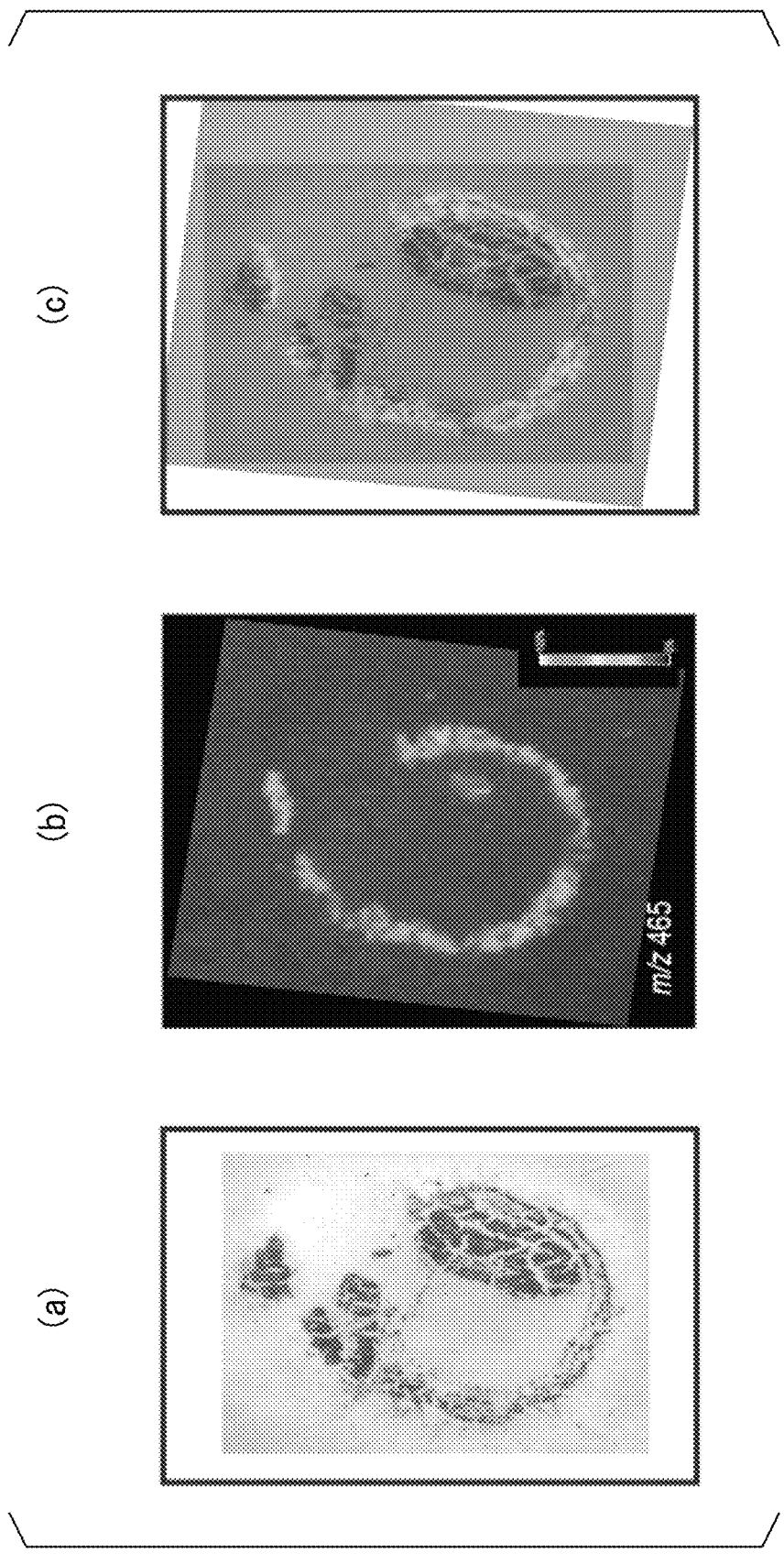

(a) to (c) of FIG. 19 are photographs showing the results of Experimental Example 10.

Figure 20:
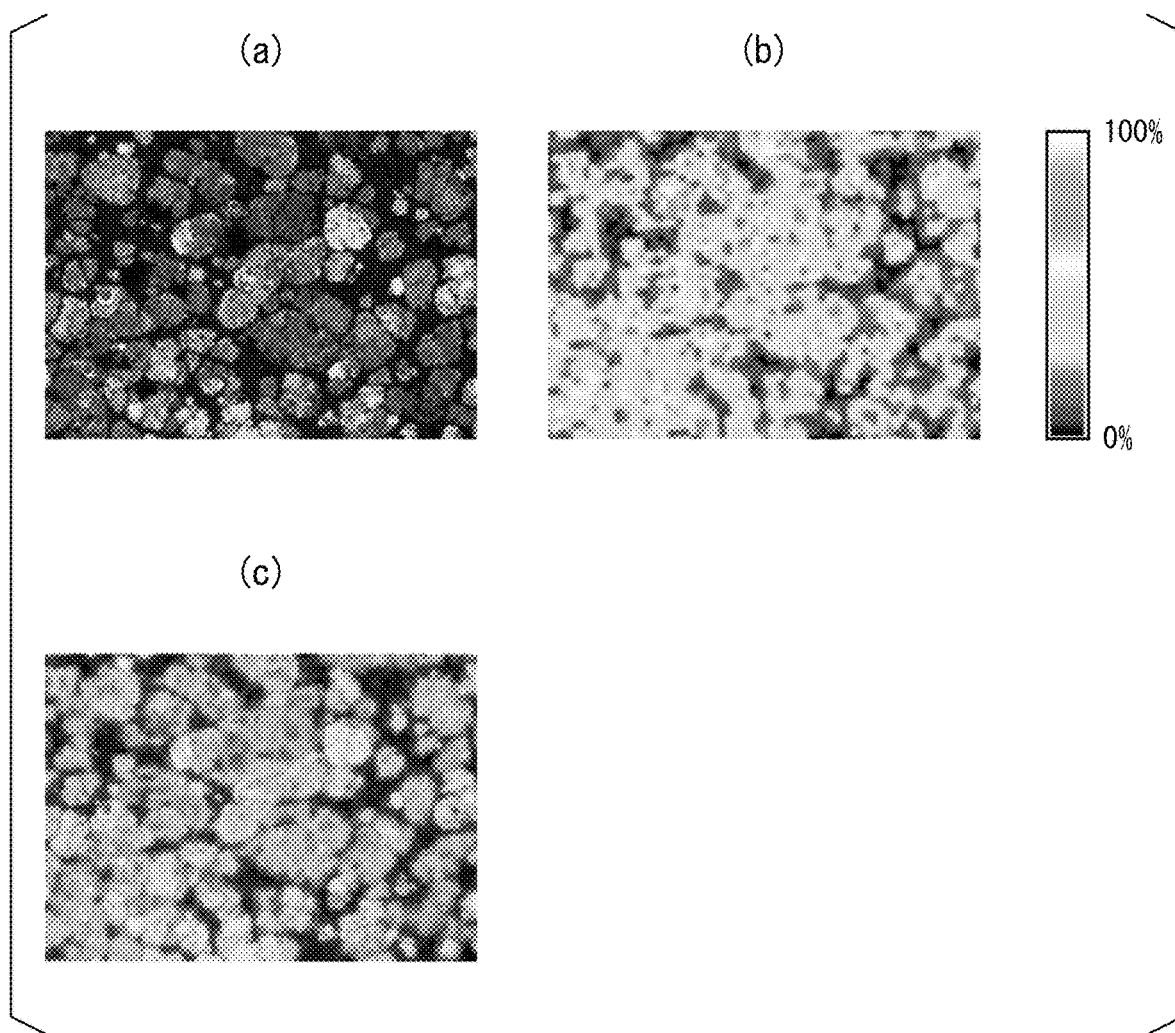

(a) to (c) of FIG. 20 are photographs showing the results of Experimental Example 11.

Figure 21:
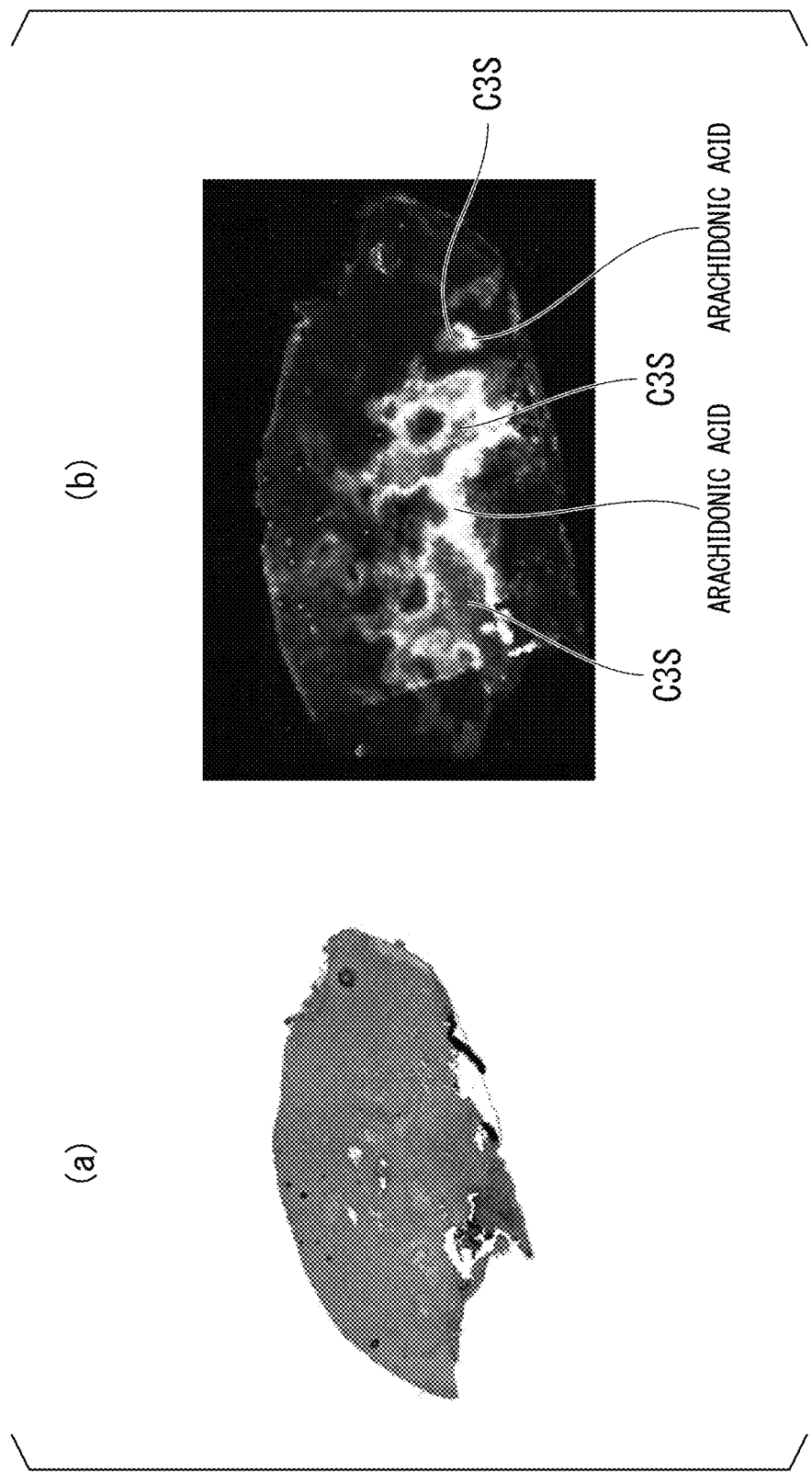

(a) and (b) of FIG. 21 are photographs showing the results of Experimental Example 12.

Figure 22:
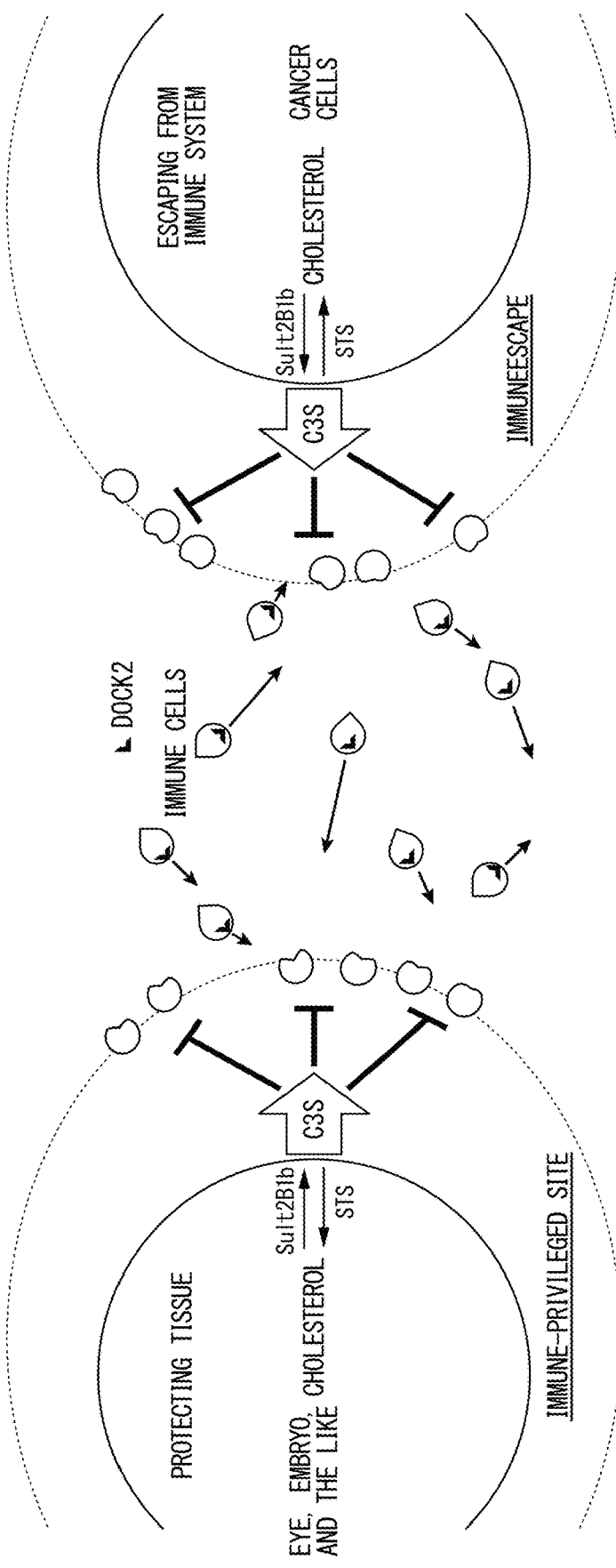

FIG. 22 is a view schematically illustrating the action of cholesterol 3-sulfate in several biological responses that are clarified this time by the inventors of the present invention.

DESCRIPTION OF EMBODIMENTS

The immune response is an essential defense mechanism for the biological body against infection, and immune cells patrol all the time such that they promptly cope with various infection sources. The characteristics of immune cells to continuously move around the body have evolved exclusively in the immune system.

DOCK2 is a guanine nucleotide exchange factor (GEF)- and is expressed specifically in immune cells to control the immune response. DOCK2 activates Rac, which is a sort of low-molecular-weight GTP-binding proteins, and forms an actin-rich protrusion called lamelliopodium, and in this way, DOCK2 provides a driving force for cell movement.

DOCK2 has a DHR-2 domain unique to DOCK family proteins. By converting GDP-bound Rac to GTP-bound Rac through this domain, DOCK2 activates Rac.

As described later, the inventors of the present invention revealed that cholesterol 3-sulfate (hereinafter, referred to as "C3S" in some cases) is important for formation of the immune privilege. FIG. 22 is a view schematically illustrating the action of cholesterol 3-sulfate in biological responses revealed by the inventors of the present invention. For the migration and infiltration of immune cells, the action of DOCK2 is necessary. By impeding the function of DOCK2 and inhibiting the movement of immune cells, cholesterol 3-sulfate contributes to the formation of immune-privileged sites and induction of the immune evasion in cancer cells.

[The Regulatory Agent for DOCK2-Mediated Rac Activation]

The immunoregulatory agent of the present embodiment contains the agent to regulate DOCK2-mediated Rac activation (DOCK2 regulatory agent) as an active ingredient. In the present specification, regulation of Rac activation means either the inhibition of Rac activation, the acceleration of Rac activation, or the maintenance of Rac activation. For example, "inhibition of Rac activation" means that the Rac activation is completely or partially inhibited (Rac activation is inhibited). Examples of the immunoregulatory agent of the present embodiment include specific binding substances for the DHR-2 domain of DOCK2, specific binding substances for Rac, specific binding substances for cholesterol 3-sulfate, and inhibitors for enzymes that mediate sulfation or desulfation of cholesterol 3-sulfate, all of which affect the DOCK2-mediated Rac activation. The specific binding substances will be described later.

As described later in examples, for example, cholesterol 3-sulfate is a specific and potent inhibitor for DOCK2-mediated Rac activation.

[Cholesterol 3-Sulfate and Derivatives Thereof]

In an embodiment, the agent to regulate DOCK2-mediated Rac activation is a compound represented by Formula (1), a pharmacologically acceptable salt thereof, or a solvate of these. That is, in an embodiment, the present invention provides an immunoregulatory agent containing, as an active ingredient, a compound represented by Formula (1), a pharmacologically acceptable salt thereof, or a solvate of these (hereinafter, described as "cholesterol 3-sulfate or a derivative thereof" in some cases). In Formula (1), $R^1$ represents an alkyl group having 3 to 12 carbon atoms that may be linear, branched or cyclic and may be substituted or represents an aromatic group having 6 to 12 carbon atoms that may be substituted.

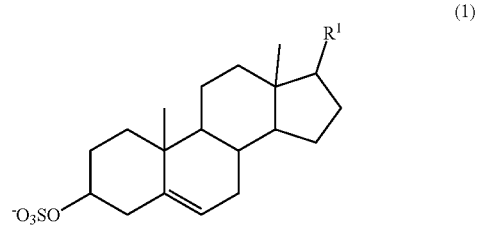

(1)

As described later in examples, the inventors of the present invention have found that cholesterol 3-sulfate represented by Formula (1) in which $R^1$ represents 1,5-dimethyl-n-hexyl group is formed in and functionally important for immune-privileged sites. In the present specification, the immune-privileged site means a site to which infiltration of immune cells is prevented. Because immune cells do no infiltrate the immune-privileged site, the immune response or the inflammatory action is inhibited at the site.

Cholesterol 3-sulfate is a compound having a steroid skeleton and known to be present in a biological body. However, the physiological function thereof is still unknown, and it has been pointed out that cholesterol 3-sulfate is likely to be a cholesterol reservoir in the blood.

By inhibiting DOCK2-mediated Rac activation, the compound represented by Formula (1) inhibits the cell migration of immune cells. It is considered that as a result, immune cells cannot infiltrate into the site where the compound represented by Formula (1) is present, and hence the immune-privileged site is formed.

The compound represented by Formula (1), a pharmacologically acceptable salt thereof, or a solvate of these can form an immune-privileged site. Accordingly, the immunoregulatory agent of the present embodiment can be referred to as an immune-privileged site-forming agent. Alternatively, the immunoregulatory agent of the present embodiment can be referred to as an immunosuppressant. It is considered that because cholesterol 3-sulfate is a compound originally present in a biological body, the immunoregulatory agent of the present embodiment causes few side effects even when administered to a biological body.

In the compound represented by Formula (1), $R^1$ is preferably a branched alkyl group or an aromatic group having 6 to 12 carbon atoms that may be substituted. Examples of substituents of $R^1$ include a hydroxyl group, an acyl group, a phosphoric acid group, a carboxyl group, an amino group, a nitro group, a thiol group, an acetamide group, a halogen atom, and the like. However, it is preferable that $R^1$ be unsubstituted. The number of carbon atoms in $R^1$ is more preferably 6 to 10, and even more preferably 7 to 9.

Examples of $R^1$ in Formula (1) include a 1,5-dimethyl-n-hexyl group, a phenyl group, a p-methoxyphenyl group, an o-butylphenyl group, an o-2-methylbutylphenyl group, and the like. In a case where $R^1$ in Formula (1) is a 1,5-dimethyl-n-hexyl group, the compound represented by Formula (1) is cholesterol 3-sulfate represented by Formula (2).

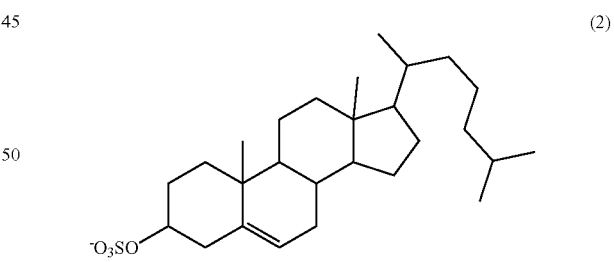

(2)

In the immunoregulatory agent of the present embodiment, the compound represented by Formula (1) may be a free compound, a pharmacologically acceptable salt, a solvate of the free compound, or a solvate of the pharmacologically acceptable salt.

Examples of the pharmacologically acceptable salt include a metal salt, an ammonium salt, an organic amine addition salt, an amino acid addition salt, and the like. More specifically, examples thereof include an inorganic acid salt such as hydrochloride, sulfate, hydrobromate, nitrate, or phosphate; an organic acid salt such as acetate, mesilate, succinate, maleate, fumarate, citrate, or tartrate; an alkali metal salt such as a sodium salt or a potassium salt; an alkali earth metal salt such as a magnesium salt or a calcium salt; a metal salt such as an aluminum salt or a zinc salt; an ammonium salt such as an ammonium salt or a tetramethylammonium salt; an organic amine addition salt such as morpholine or piperidine; an amino acid addition salt such as glycine, phenylalanine, lysine, aspartic acid, or glutamic acid; and the like.

The solvate is not particularly limited as long as it is a pharmacologically acceptable solvate, and examples thereof include a hydrate, an organic solvate, and the like.

By administering the immunoregulatory agent of the present embodiment into the tissues of transplanted organs in the form of a slow-release preparation, a rejection reaction can be suppressed. Alternatively, by administering the immunoregulatory agent of the present embodiment to patients with immunological diseases such as rheumatoid arthritis, uveitis, and multiple sclerosis resulting from an excessive immune response, the disease development can be treated.

[Specific Binding Substance Against Cholesterol 3-Sulfate or Salt Thereof]

In an embodiment, the immunoregulatory agent for DOCK2-mediated Rac activation is a specific binding substance against cholesterol 3-sulfate or a salt thereof. That is, in an embodiment, the present invention provides an immunoregulatory agent containing, as an active ingredient, a specific binding substance against cholesterol 3-sulfate or a salt thereof. Examples of the salt of cholesterol 3-sulfate include the same ones as those exemplified above as salts of the compound represented by Formula (1).

The immunoregulatory agent of the present embodiment can impede the function of cholesterol 3-sulfate in a biological body by binding to cholesterol 3-sulfate. Alternatively, the immunoregulatory agent of the present embodiment can reduce the concentration of cholesterol 3-sulfate in a biological body by adsorbing cholesterol 3-sulfate. As a result, the immune privilege formed due to the presence of cholesterol 3-sulfate can be removed. Accordingly, the immunoregulatory agent of the present embodiment can also be referred to as an immune privilege-removing agent. Alternatively, the immunoregulatory agent of the present embodiment can be referred to as an immune evasion-releasing agent. A dissociation constant Kd of the specific binding substance and cholesterol 3-sulfate is, for example, preferably equal to or smaller than $10^{-7}$ M, more preferably equal to or smaller than $10^{-8}$ M, and even more preferably equal to or smaller than $10^{-9}$ M.

In a case where the immune privilege is released by the immunoregulatory agent of the present embodiment, immune cells infiltrate the region, and hence the immune response is activated. Consequently, the immunoregulatory agent of the present embodiment can also be referred to as an immunostimulant.

As described later in examples, the inventors of the present invention have found that cholesterol 3-sulfate is abundantly present in a cancer tissue and forms an immune-privileged site. Accordingly, by releasing the immune privilege from the cancer tissue using the immunoregulatory agent of the present embodiment, it is possible to stimulate the immune response against the cancer tissue and to treat the cancer.

In the present specification, examples of the specific binding substance include an antibody, an antibody fragment, an aptamer, a low-molecular-weight compound, and the like. The antibody can be prepared, for example, by immunizing an animal such as a mouse with an antigen. Alternatively, the antibody can be prepared by screening of an antibody library such as a phage library and the like. Herein, it is preferable to use cholesterol 3-sulfate or a salt thereof as an antigen. The antigen may be in the form of a hapten.

Examples of the antibody fragment include Fv, Fab, scFv, and the like. The antibody or the antibody fragment described above may be polyclonal or monoclonal. Furthermore, for example, a compound such as polyethylene glycol may be bound to the antibody or the antibody fragment. By covalently attaching polyethylene glycol to the antibody or the antibody fragment, for example, the stability of the antibody or the antibody fragment in the blood can be improved.

The aptamer is a substance that can specifically bind to a labeled substance. Examples of the aptamer include a nucleic acid aptamer, a peptide aptamer, and the like. The nucleic acid aptamer that can specifically bind to cholesterol 3-sulfate or a salt thereof can be sorted out, for example, by a systematic evolution of ligand by exponential enrichment (SELEX) method and the like. The peptide aptamer that can specifically bind to cholesterol 3-sulfate or a salt thereof can be sorted out, for example, by a Two-hybrid method using yeast and the like.

As the specific binding substance, in addition to the above, those screened out of a compound library which showed binding properties against a target substance may be used.

The aforementioned specific binding substance may be a protein which has an amino acid sequence described in SEQ ID NO: 1 or a protein which has an amino acid sequence formed by the deletion, substitution, or addition of one or several amino acids in the amino acid sequence described in SEQ ID NO: 1 and exhibits binding activity against cholesterol 3-sulfate or a salt thereof (hereinafter, this protein will be referred to as "mutant of the protein having the amino acid sequence described in SEQ ID NO: 1" in some cases). In the present specification, "one or several" means that the number of amino acids is 1 to 20, 1 to 10, 1 to 5, or 1 to 3, for example.

The DHR-2 domain of DOCK2 includes regions called a lobe A, a lobe B, and a lobe C. The amino acid sequence described in SEQ ID NO: 1 is an amino acid sequence of a protein including the lobe B and the lobe C of the DHR-2 domain of human DOCK2. More specifically, the lobe B includes the $1^4$ to $141^{st}$ amino acids in SEQ ID NO: 1, and the lobe C includes the $142^{nd}$ to $427^{th}$ amino acids in SEQ ID NO: 1.

As described later in examples, the inventors of the present invention have found that the protein having the amino acid sequence described in SEQ ID NO: 1 specifically binds to cholesterol 3-sulfate. Accordingly, the protein having an amino acid sequence described in SEQ ID NO: 1 or a mutant thereof can be used as a specific binding substance against cholesterol 3-sulfate. Furthermore, the protein having the amino acid sequence described in SEQ ID NO: 1 or a mutant thereof may be covalently attached to a compound such as polyethylene glycol such that the stability thereof in the blood is improved.

[Expression Vector of Protein Having Amino Acid Sequence Described in SEQ ID NO: 1]

In an embodiment, the regulatory agent for DOCK2-mediated Rac activation is an expression vector of the protein which has the amino acid sequence described in SEQ ID NO: 1 or an expression vector of the protein which has an amino acid sequence formed by the deletion, substitution, or addition of one or several amino acids in the amino acid sequence described in SEQ ID NO: 1 and exhibits binding activity against cholesterol 3-sulfate or a salt thereof. That is, in an embodiment, the present invention provides an immunoregulatory agent containing, as an active ingredient, an expression vector of the protein which has the amino acid sequence described in SEQ ID NO: 1 or an expression vector of the protein which has an amino acid sequence formed by the deletion, substitution, or addition of one or several amino acids in the amino acid sequence described in SEQ ID NO: 1 and exhibits binding activity against cholesterol 3-sulfate or a salt thereof.

By administering the expression vector of the present embodiment to a biological body, the protein having the amino acid sequence described in SEQ ID NO: 1 or a mutant thereof can be expressed. The protein having the amino acid sequence described in SEQ ID NO: 1 or a mutant thereof that is expressed from the expression vector functions as a specific binding substance against cholesterol 3-sulfate or a salt thereof as described above. Accordingly, the immunoregulatory agent of the present embodiment can also be referred to as an immune privilege-removing agent. Alternatively, the immunoregulatory agent of the present embodiment can be referred to as an immune evasion-releasing agent. As another option, the immunoregulatory agent of the present embodiment can be referred to as an immunostimulant.

The expression vector is not particularly limited as long as it can express the protein having the amino acid sequence described in SEQ ID NO: 1 or a mutant thereof in a cell as a target of administration. For example, it is possible to use an *E. coli*-derived vector such as pBR322, pBR 325, pUC12, or pUC13; a *Bacillus subtilis*-derived vector such as pUB110, pTP5, or pC194; an yeast-derived vector such as pSH19 or pSH15; a bacteriophage such as a λ-phage; viruses such as an adenovirus, an adeno-associated virus, a lentivirus, a vaccinia virus, or a baculovirus; vectors obtained by modifying these; and the like.

In the expression vector, a promoter for expressing the protein having an amino acid sequence described in SEQ ID NO: 1 or a mutant thereof is not particularly limited, and examples thereof include an EF1α promoter, an SRα promoter, an SV40 promoter, an LTR promoter, a cytomegalovirus (CMV) promoter, an HSV-tk promoter, and the like.

The expression vector may further have a multicloning site, an enhancer, a splicing signal, a poly A addition signal, a selective marker, a replication origin, and the like.

[Sulfotransferase Family Cytosolic 2B Member 1 Isoform b (SULT2B1b) Protein, Expression Vector Thereof, Expression Inhibition Substance, and Inhibitor]

In an embodiment, the regulatory agent for DOCK2-mediated Rac activation is a protein which has an amino acid sequence described in SEQ ID NO: 2; a protein which has an amino acid sequence formed by the deletion, substitution, or addition of one or several amino acids in the amino acid sequence described in SEQ ID NO: 2 and has an activity to add a sulfonic acid group to the hydroxyl group at position 3 of cholesterol; an expression vector of the protein which has the amino acid sequence described in SEQ ID NO: 2; an expression vector of the protein which has the amino acid sequence formed by the deletion, substitution, or addition of one or several amino acids in the amino acid sequence described in SEQ ID NO: 2 and has an activity to add a sulfonic acid group to the hydroxyl group at position 3 of cholesterol; siRNA, shRNA, miRNA, ribozyme, or an antisense nucleic acid inhibiting the expression of the protein which has the amino acid sequence described in SEQ ID NO: 2; or an inhibitor of the protein which has the amino acid sequence described in SEQ ID NO: 2.

That is, in an embodiment, the present invention provides an immunoregulatory agent containing, as an active ingredient, a protein which has an amino acid sequence described in SEQ ID NO: 2; a protein which has an amino acid sequence formed by the deletion, substitution, or addition of one or several amino acids in the amino acid sequence described in SEQ ID NO: 2 and has an activity to add a sulfonic acid group to the hydroxyl group at position 3 of cholesterol (hereinafter, referred to as "SULT2B1b protein or a mutant thereof" in some cases); an expression vector of the protein which has the amino acid sequence described in SEQ ID NO: 2, an expression vector of the protein which has the amino acid sequence formed by the deletion, substitution, or addition of one or several amino acids in the amino acid sequence described in SEQ ID NO: 2 and has an activity to add a sulfonic acid group to the hydroxyl group at position 3 of cholesterol; siRNA, shRNA, miRNA, ribozyme, or an antisense nucleic acid inhibiting the expression of the protein which has the amino acid sequence described in SEQ ID NO: 2; or an inhibitor of the protein which has the amino acid sequence described in SEQ ID NO: 2.

The SULT2B1b protein is an enzyme which has an activity to add a sulfonic acid group to the hydroxyl group at position 3 of cholesterol. Accordingly, in a case where the SULT2B1b protein or a mutant thereof is administered to a biological body, it is possible to generate cholesterol 3-sulfate and form an immune-privileged site.

Therefore, the immunoregulatory agent containing, as an active ingredient, the SULT2B1b protein or a mutant thereof can also be referred to as an immune-privileged site-forming agent. Alternatively, the immunoregulatory agent containing, as an active ingredient, the SULT2B1b protein or a mutant thereof can be referred to as an immunosuppressant. The SULT2B1b protein or a mutant thereof may covalently attached, for example, to a compound such as polyethylene glycol such that the stability thereof in the blood is improved.

The immunoregulatory agent of the present embodiment may contain, as an active ingredient, an expression vector of the SULT2B1b protein or a mutant thereof. Examples of the expression vector include the same ones as those described above. In a case where the expression vector of the present embodiment is administered to a biological body, the SULT2B1b protein or a mutant thereof can be expressed. The SULT2B1b protein or a mutant thereof expressed from the expression vector can form an immune-privileged site by generating cholesterol 3-sulfate as described above.

Accordingly, the immunoregulatory agent containing, as an active ingredient, the expression vector of the SULT2B1b protein or a mutant thereof can also be referred to as an immune-privileged site-forming agent. Alternatively, the immunoregulatory agent containing, as an active ingredient, the expression vector of the SULT2B1b protein or a mutant thereof can be referred to as an immunosuppressant.

The immunoregulatory agent containing, as an active ingredient, the expression vector of the SULT2B1b protein or a mutant thereof is expressed, for example, by being transduced into a transplanted organ prepared by the technology of regenerative medicine. In this way, the immunoregulatory agent can grant an immune-privilege in the transplanted organ and inhibit a rejection reaction.

Alternatively, by administering the immunoregulatory agent of the present embodiment to patients with immunological diseases such as rheumatoid arthritis, uveitis, and multiple sclerosis resulting from an excessive immune response, the disease development can be treated.

The immunoregulatory agent of the present embodiment may contain, as an active ingredient, siRNA, shRNA, ribozyme, or an antisense nucleic acid which inhibits the expression of the SULT2B1b protein. In the present specification, siRNA, shRNA, miRNA, ribozyme, and the antisense nucleic acid will be collectively called "expression inhibition substance" in some cases. By administering siRNA, shRNA, miRNA, ribozyme, or the antisense nucleic acid to a biological body, the expression of the SULT2B1b protein can be inhibited. As a result, it is possible to inhibit the generation of cholesterol 3-sulfate and to inhibit the formation of an immune-privileged site.

Consequently, the immunoregulatory agent containing, as an active ingredient, siRNA, shRNA, miRNA, ribozyme, or the antisense nucleic acid which inhibits the expression of the SULT2B1b protein, can also be referred to as an immune-privileged site formation inhibitor. Alternatively, the immunoregulatory agent containing, as an active ingredient, siRNA, shRNA, miRNA, ribozyme, or the antisense nucleic acid which inhibits the expression of the SULT2B1b protein, can be referred to as an immunostimulant.

For example, through systemic administration or local administration to a cancer tissue, the immunoregulatory agent containing, as an active ingredient, siRNA, shRNA, miRNA, ribozyme, or the antisense nucleic acid which inhibits the expression of the SULT2B1b protein releases the immune privilege in the cancer tissue. In this way, the immunoregulatory agent can stimulate the immune response against the cancer tissue and treat the cancer.

The siRNA (small interfering RNA) is low-molecular-weight double-stranded RNA with 21 to 23 base pairs that is used for gene silencing caused by RNA interference. The siRNA introduced into a cell binds to an RNA-induced silencing complex (RISC). The complex binds to mRNA having a complementary sequence for siRNA and cleaves the mRNA. In this way, sequence-specific inhibition of gene expression is achieved.

The siRNA can be prepared by synthesizing oligonucleotides as a sense strand and an antisense strand by using an automatic DNA/RNA-synthesizing machine, denaturing the oligonucleotides at a temperature of 90° C. to 95° C. for about 1 minute in, for example, an appropriate annealing buffer solution, and then annealing the oligonucleotides at a temperature of 30° C. to 70° C. for about 1 to 8 hours.

Specific examples of the base sequence of the sense strand of the siRNA which inhibits the expression of a human SULT2B1b protein include base sequences described in SEQ ID NOS: 4 to 7 and the like.

The shRNA (short hairpin RNA) is a hairpin-type RNA sequence used for gene silencing caused by RNA interference. The shRNA may be expressed in a U6 promoter or an H1 promoter by being introduced into a cell by using a vector. Alternatively, the shRNA may be prepared by synthesizing an oligonucleotide having an shRNA sequence by using an automatic DNA/RNA-synthesizing machine and causing the oligonucleotide to be annealed by itself by using the same method as that used for the siRNA. The hairpin structure of the shRNA introduced into a cell is cleaved to form siRNA and binds to the RNA-induced silencing complex (RISC). The complex binds to mRNA having a complementary sequence for siRNA and cleaves the mRNA. In this way, sequence-specific inhibition of gene expression is achieved.

Specific examples of the base sequence of the shRNA which inhibits the expression of the human SULT2B1b protein includes the base sequences described in SEQ ID NOS: 8 to 10 and the like.

The miRNA (microRNA) is a functional nucleic acid which is genomically encoded, passes through a multi-stage generation process, and finally becomes microRNA including about 20 bases. The miRNA is classified as functional non-coding RNA (ncRNA: generic name of RNA which is not translated into a protein) and plays a role of controlling the expression of other genes, which is an important role in a vital phenomenon. By administering the miRNA having a specific base sequence to a biological body, the expression of the human SULT2B1b protein can be inhibited.

The ribozyme is RNA having catalytic activity. The ribozyme has various activities, and by the research on the ribozyme as an RNA cleaving enzyme, a ribozyme for site-specific cleaving of RNA can be designed. The ribozyme may be a large molecule including 400 or more nucleotides, such as a group I intron type or M1RNA included in RnaseP, or a molecule including about 40 nucleotides called a hammerhead type, a hairpin type, or the like.

The antisense nucleic acid is a complementary nucleic acid for a target sequence. The antisense nucleic acid inhibits the initiation of transcription by forming a triple strand, inhibits transcription by forming a hybrid with a site where an open-loop structure is locally formed by an RNA polymerase, inhibits transcription by forming a hybrid with RNA which is in the process of synthesis, inhibits splicing by forming a hybrid at a bonding point between the intron and the exon, inhibits splicing by forming a hybrid with a site where a spliceosome is formed, inhibits the transition to the cytoplasm from a nucleus by forming a hybrid with mRNA, inhibits splicing by forming a hybrid with a capping site or a poly (A) addition site, inhibits the initiation of translation by forming a hybrid with a translation initiation factor-binding site, inhibits translation by forming a hybrid with a polysome-binding site in the vicinity of the start codon, hinders peptide chain elongation by forming a hybrid with an mRNA translation region or a ribosome-binding site, and inhibits gene expression by forming a hybrid with a site where a nucleic acid and a protein interact with each other. In this way, the antisense nucleic acid can inhibit the expression of a target gene.

In the present embodiment, siRNA, shRNA, miRNA, ribozyme, and the antisense nucleic acid may be chemically modified in various ways such that the stability or the activity thereof is improved. For example, in order to prevent the decomposition caused by a hydrolase such as nuclease, a phosphoric acid residue may be substituted, for example, with a chemically modified phosphoric acid residue such as phosphorothioate (PS), methyl phosphonate, or phosphorodithioate. Furthermore, at least a portion thereof may be constituted with a nucleic acid analog such as a peptide nucleic acid (PNA).

The immunoregulatory agent of the present embodiment may contain, as an active ingredient, the inhibitor of the SULT2B1b protein. The inhibitor of the SULT2B1b protein is preferably a low-molecular-weight compound. By administering the inhibitor of the SULT2B1b protein to a biological body, the activity of the SULT2B1b protein can be inhibited. As a result, the generation of cholesterol 3-sulfate can be inhibited, and the formation of an immune-privileged site can be inhibited.

Accordingly, the immunoregulatory agent containing, as an active ingredient, the inhibitor of the SULT2B1b protein can also be referred to as an immune-privileged site formation inhibitor. Alternatively, the immunoregulatory agent containing, as an active ingredient, the inhibitor of the SULT2B1b protein can be referred to as an immunostimulant.

For example, through systemic administration or local administration to a cancer tissue, the immunoregulatory agent containing, as an active ingredient, the inhibitor of the SULT2B1b protein inhibits formation of immune privilege sites in the cancer tissue. In this way, the immunoregulatory agent can stimulate the immune response against the cancer tissue and treat the cancer.

[Steryl-Sulfatase (STS) Protein, Expression Vector Thereof, Expression Inhibition Substance, and Inhibitor]

In an embodiment, the immunoregulatory agent for DOCK2-mediated Rac activation is a protein which has an amino acid sequence described in SEQ ID NO: 3, a protein which has an amino acid sequence formed by the deletion, substitution, or addition of one or several amino acids in the amino acid sequence described in SEQ ID NO: 3 and acts to remove a sulfonic acid group of cholesterol 3-sulfate; an expression vector of the protein which has the amino acid sequence described in SEQ ID NO: 3, an expression vector of the protein which has the amino acid sequence formed by the deletion, substitution, or addition of one or several amino acids in the amino acid sequence described in SEQ ID NO: 3 and acts to remove a sulfonic acid group of cholesterol 3-sulfate; siRNA, shRNA, miRNA, ribozyme, or an antisense nucleic acid inhibiting the expression of the protein whose amino acid sequence is described in SEQ ID NO: 3; or an inhibitor of the protein which has the amino acid sequence described in SEQ ID NO: 3.

That is, in an embodiment, the present invention provides an immunoregulatory agent containing, as an active ingredient, a protein which has an amino acid sequence described in SEQ ID NO: 3, a protein which has an amino acid sequence formed by the deletion, substitution, or addition of one or several amino acids in the amino acid sequence described in SEQ ID NO: 3 and acts to remove a sulfonic acid group of cholesterol 3-sulfate; an expression vector of the protein which has the amino acid sequence described in SEQ ID NO: 3, an expression vector of the protein which has the amino acid sequence formed by the deletion, substitution, or addition of one or several amino acids in the amino acid sequence described in SEQ ID NO: 3 and acts to remove a sulfonic acid group of cholesterol 3-sulfate; siRNA, shRNA, miRNA, ribozyme, or an antisense nucleic acid inhibiting the expression of the protein whose amino acid sequence is described in SEQ ID NO: 3, or an inhibitor for the protein whose amino acid sequence is described in SEQ ID NO: 3.

The amino acid sequence described in SEQ ID NO: 3 is the same as that of a human STS protein. The STS protein is an enzyme which acts to remove a sulfonic acid group attached to a hydroxyl group of steroid skeleton. Accordingly, by administering the STS protein or a mutant thereof to a biological body, it is possible to remove a sulfonic acid group of cholesterol 3-sulfate and to generate cholesterol. As a result, the concentration of cholesterol 3-sulfate in the biological body can be reduced. Consequently, the immune privilege that is formed due to the presence of cholesterol 3-sulfate can be removed.

Therefore, the immunoregulatory agent containing, as an active ingredient, the STS protein or a mutant thereof can also be referred to as an immune privilege-removing agent. Alternatively, the immunoregulatory agent containing, as an active ingredient, the STS protein or a mutant thereof can be referred to as an immune evasion-releasing agent. As another option, the immunoregulatory agent containing, as an active ingredient, the STS protein or a mutant thereof can be referred to as an immunostimulant. The STS protein or a mutant thereof may be attached, for example, to a compound such as polyethylene glycol such that the stability thereof in the blood is improved.

For example, through systemic administration or local administration to a cancer tissue, the immunoregulatory agent containing, as an active ingredient, the STS protein or a mutant thereof removes the immune privilege from the cancer tissue. In this way, the immunoregulatory agent can stimulate the immune response against the cancer tissue and treat the cancer.

The immunoregulatory agent of the present embodiment contains, as an active ingredient, the expression vector of the STS protein or a mutant thereof. Examples of the expression vector include the same ones as those described above. By administering the expression vector of the present embodiment to a biological body, the STS protein or a mutant thereof can be expressed. The STS protein or a mutant thereof expressed from the expression vector converts cholesterol 3-sulfate into cholesterol and reduces the concentration of cholesterol 3-sulfate in the biological body as described above. In this way, the STS protein or a mutant thereof can remove the immune privilege that is formed due to the presence of cholesterol 3-sulfate.

Accordingly, the immunoregulatory agent containing, as an active ingredient, the expression vector of the STS protein or a mutant thereof can also be referred to as an immune privilege-removing agent. Alternatively, the immunoregulatory agent containing, as an active ingredient, the expression vector of the STS protein or a mutant thereof can be referred to as an immune evasion-releasing agent. As another option, the immunoregulatory agent containing, as an active ingredient, the expression vector of the STS protein or a mutant thereof can be referred to as an immunostimulant.

For example, through systemic administration or local administration to a cancer tissue, the immunoregulatory agent containing, as an active ingredient, the expression vector of the STS protein or a mutant thereof removes the immune privilege from the cancer tissue. In this way, the immunoregulatory agent can stimulate the immune response against the cancer tissue and treat the cancer.

The immunoregulatory agent of the present embodiment may contain, as an active ingredient, siRNA, shRNA, miRNA, ribozyme, or the antisense nucleic acid which inhibits the expression of the STS protein. By administering siRNA, shRNA, miRNA, ribozyme, or an antisense nucleic acid to a biological body, the expression of the STS protein can be inhibited. As a result, it is possible to inhibit removal of a sulfonic acid group from cholesterol 3-sulfate and to increase the concentration of cholesterol 3-sulfate in the biological body such that the immune-privileged site is formed or maintained.

Accordingly, the immunoregulatory agent containing, as an active ingredient, siRNA, shRNA, miRNA, ribozyme, or the antisense nucleic acid which inhibits the expression of the STS protein can also be referred to as an immune-privileged site-forming agent. Alternatively, the immunoregulatory agent containing, as an active ingredient, siRNA, shRNA, miRNA, ribozyme, or the antisense nucleic acid which inhibits the expression of the STS protein can be referred to as an immune privilege-maintaining agent. As another option, the immunoregulatory agent containing, as an active ingredient, siRNA, shRNA, miRNA, ribozyme, or the antisense nucleic acid-which inhibits the expression of the STS protein can be referred to as an immune evasion-maintaining agent. Or, the immunoregulatory agent containing, as an active ingredient, siRNA, shRNA, miRNA, ribozyme, or the antisense nucleic acid which inhibits the expression of the STS protein can be referred to as an immunosuppressant. The siRNA, shRNA, miRNA, ribozyme, and antisense nucleic acid are the same as those described above.

Specific examples of the base sequence of the sense chain of the siRNA which inhibits the expression of the human STS protein include the base sequences described in SEQ ID NOS: 11 to 14 and the like.

Specific examples of the base sequence of the shRNA which inhibits the expression of the human STS protein include base sequences described in SEQ ID NOS: 15 to 17 and the like.

By administering the immunoregulatory agent containing, as an active ingredient, siRNA, shRNA, miRNA, ribozyme, or the antisense nucleic acid which inhibits the expression of the STS protein into the tissues of transplanted organs in the form of a slow-release preparation together with, for example, the aforementioned cholesterol 3-sulfate or a derivative thereof, an immune-privileged site can be easily formed, and a rejection reaction can be inhibited.

The immunoregulatory agent of the present embodiment may contain, as an active ingredient, the inhibitor of the STS protein. The inhibitor of the STS protein is preferably a low-molecular-weight compound. By administering the inhibitor of the STS protein to a biological body, the activity of the STS protein can be inhibited. As a result, it is possible to inhibit removal of a sulfonic acid group from cholesterol 3-sulfate and to increase the concentration of cholesterol 3-sulfate in a biological body such that the immune-privileged site is formed or maintained.

Accordingly, the immunoregulatory agent containing, as an active ingredient, the inhibitor of the STS protein can also be referred to as an immune-privileged site-forming agent.

Alternatively, the immunoregulatory agent containing, as an active ingredient, the inhibitor of the STS protein can be referred to as an immune privilege-maintaining agent. As another option, the immunoregulatory agent containing, as an active ingredient, the inhibitor of the STS protein can be referred to as an immune evasion-maintaining agent. Or, the immunoregulatory agent containing, as an active ingredient, the inhibitor of the STS protein can be referred to as an immunosuppressant.

Examples of the inhibitor for the STS protein include 667 COUMATE, STX213, KW-2581, STX681, YM511, and the like.

[Pharmaceutical Composition]

The aforementioned immunoregulatory agent may be administered as it is or may be administered after being made into a preparation as a pharmaceutical composition mixed with a pharmacologically accepted carrier.

The pharmaceutical composition may be made into a preparation for oral administration such as a tablet, a capsule, an elixir, or a microcapsule, or may be made into a preparation for parenteral administration such as an injection, an ointment, or a patch.

Examples of the pharmacologically acceptable carrier include a solvent such as sterile water or physiological saline; a binder such as gelatin, corn starch, tragacanth gum, or gum Arabic; an excipient such as crystalline cellulose; a bulking agent such as corn starch, gelatin, or alginic acid; and the like.

The pharmaceutical composition may contain additives. Examples of the additives include a lubricant such as magnesium stearate; a sweetener such as sucrose, lactose, or saccharin; a flavoring agent such as peppermint or Akamono oil; a stabilizer such as benzyl alcohol or phenol; a buffer such as phosphate or sodium acetate; a solubilizing agent such as benzyl benzoate or benzyl alcohol; an antioxidant; a preservative; a surfactant; an emulsifier; and the like.

By appropriately combining the pharmaceutical composition with the carrier and the additives described above and mixing them together at a unit dose required for making a drug in a generally acceptable way, the pharmaceutical composition can be made into a preparation.

In a case where the pharmaceutical composition is an injection, examples of the solvent for the injection include isotonic solutions containing an adjuvant such as physiological saline, glucose, D-sorbitol, D-mannose, D-mannitol, or sodium chloride. The solvent for the injection may contain an alcohol such as ethanol; a polyalcohol such as propylene glycol or polyethylene glycol; a nonionic surfactant such as Polysorbate 80 (trademark) or HCO-50; and the like.

The immunoregulatory agent is administered to patients by the methods known to those skilled in the related art by means of intra-arterial injection, intravenous injection, subcutaneous injection, intranasal administration, transbronchial administration, intramuscular administration, transdermal administration, or oral administration.

The dose of the immunosuppressant varies with the symptom. However, in a case where the immunosuppressant is given by oral administration, generally, a daily dose for an adult (body weight: 60 kg) is 0.1 to 100 mg, 1 to 50 mg, 1 to 20 mg, or the like.

In a case where the immunoregulatory agent is given by parenteral administration, a single dose thereof varies with the administration object, the target organ, the symptom, and the administration method. However, provided that the immunoregulatory agent is administered as an injection, for example, the agent is administered to an adult (body weight: 60 kg) at a daily dose of about 0.01 to 30 mg, 0.1 to 20 mg, or 0.1 to 10 mg by means of intravenous injection or local injection.

Other Embodiments

In an embodiment, the present invention provides an immunoregulatory method including administering cholesterol 3-sulfate or a derivative thereof, a specific binding substance against cholesterol 3-sulfate or a derivative thereof, an expression vector of a protein having an amino acid sequence described in SEQ ID NO: 1 or a mutant thereof, the SULT2B1b protein or a mutant thereof, an expression vector of the SULT2B1b protein or a mutant thereof, an inhibitory substance of SULT2B1b protein expression, an inhibitor of the SULT2B1b protein, an expression vector of the STS protein or a mutant thereof, an inhibitory substance of STS protein expression inhibition substance, or an inhibitor of the STS protein to a patient or an affected animal in need of treatment at an effective dose.

In an embodiment, the present invention provides a method for inhibiting a rejection reaction of a transplanted organ, including a step of administering cholesterol 3-sulfate or a derivative thereof, the SULT2B1b protein or a mutant thereof, an expression vector of the SULT2B1b protein or a mutant thereof, an inhibitory substance of STS protein expression inhibition substance, or an inhibitor of the STS protein to a patient or an affected animal in need of treatment at an effective dose.

In an embodiment, the present invention provides a method for treating cancer, including administering a specific binding substance against cholesterol 3-sulfate or a derivative thereof, an expression vector of a protein having an amino acid sequence described in SEQ ID NO: 1 or a mutant thereof, an inhibitory substance of SULT2B1b protein expression, an inhibitor of an SULT2B1b protein, or an expression vector of the STS protein or a mutant thereof to a patient or an affected animal in need of treatment at an effective dose.

In an embodiment, the present invention provides the followings for immune regulation: cholesterol 3-sulfate or a derivative thereof, a specific binding substance against cholesterol 3-sulfate or a derivative thereof, an expression vector of a protein having an amino acid sequence described in SEQ ID NO: 1 or a mutant thereof, an SULT2B1b protein or a mutant thereof, an expression vector of the SULT2B1b protein or a mutant thereof, an inhibitory substance of SULT2B1b protein expression, an inhibitor of the SULT2B1b protein, an expression vector of an STS protein or a mutant thereof, an inhibitory substance of STS protein expression, or an inhibitor of the STS protein.

In an embodiment, the present invention provides the use of cholesterol 3-sulfate or a derivative thereof, a specific binding substance against cholesterol 3-sulfate or a derivative thereof, an expression vector of a protein having an amino acid sequence described in SEQ ID NO: 1 or a mutant thereof, an SULT2B1b protein or a mutant thereof, an expression vector of the SULT2B1b protein or a mutant thereof, an inhibitory substance of SULT2B1b protein expression, an inhibitor of the SULT2B1b protein, an expression vector of an STS protein or a mutant thereof, an inhibitory substance of STS protein expression, or an inhibitor of the STS protein for manufacturing an immunoregulatory agent.

EXAMPLES

Nest, the present invention will be more specifically explained by the examples described below, but the present invention is not limited to the following examples.

Experimental Example 1

(Examination on Selectivity of Guanine Nucleotide Exchange Factor (GEF) Activity Inhibition Effect by Cholesterol 3-Sulfate)

Figure 1:
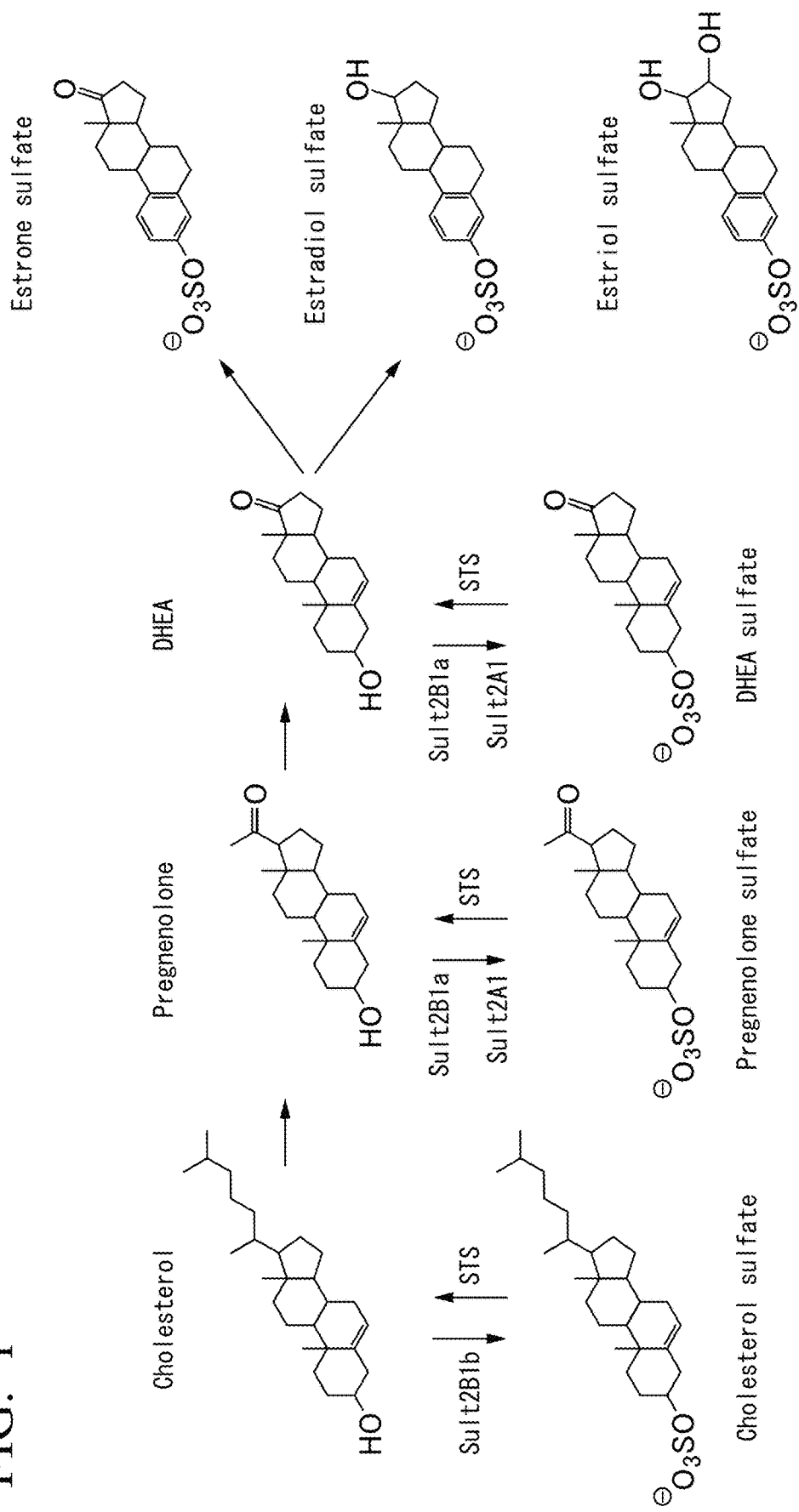
FIG. 1 is a view showing schematic representation for steroid sulfonation and de-conjugation pathway.

FIG. 1 is a view showing schematic representation for steroid sulfonation and de-conjugation pathway. By the action of an SULT2B1b enzyme, a sulfonic acid group is added to the hydroxyl group at position 3 of steroid, and as a result, cholesterol 3-sulfate (described as Cholesterol sulfate in the drawing) is biosynthesized. On the other hand, by the action of an STS enzyme, a sulfonic acid group of cholesterol 3-sulfate is removed, and as a result, cholesterol is generated.

The selectivity of the effect of inhibiting the GEF of DOCK2 by cholesterol 3-sulfate was examined. All of DOCK2, Trio, and Tiam are GEFs activating Rac. In the presence of serially diluted cholesterol 3-sulfate, the Rac activation ability of a DOCK2 protein, a Trio protein, and a Tiam protein was measured by in-vitro GEF assay. For the in-vitro GEF assay, a labeled GTP (trade name, "Bodipy-FL-GTP", manufactured by Invitrogen) was used, because it has a property of increasing fluorescence intensity when binds to Rac by the action of GEF.

More specifically, first, by using a pET28a expression vector, each of polypeptide fragments corresponding to a DHR-2 domain including the lobe B and the lobe C of DOCK2 and a DH-PH domain of the Trio protein and the Tiam protein was expressed in an $E.\ coli$ Arctic express DE3 strain as a recombinant strain in which a Histidine-SUMO tag was fused with the N terminus thereof (expression was induced overnight at 16° C. in the presence of 0.5 mM IPTG). Then, the collected $E.\ coli$ was suspended in phosphate buffer (PBS)-0.5 mM EDTA-5 mM 2-mercaptoethanol and subjected to ultrasonic disintegration. Thereafter, from the supernatant, the respective proteins were purified using a Ni-NTA affinity column.

Meanwhile, by using a pGEX-6P-1 expression vector, Rac was expressed in an $E.\ coli$ BL21 DE3 strain as a recombinant protein in which a GST tag was fused with the N terminus (expression was induced overnight at 25° C. in the presence of 0.5 mM IPTG). The collected $E.\ coli$ was suspended in PBS-1 mM EDTA-5 mM 2-mercaptoethanol and subjected to ultrasonic disintegration. Then, from the supernatant, the protein was purified using a Glutathione Sepharose 4B affinity column.

Subsequently, in a reaction solution A (20 mM MES-NaOH-150 mM NaCl-10 mM $MgCl_2$-20 µM GDP, pH 7.0), each of the prepared GEFs (DHR-2 domain or DH-PH domain) was incubated for 20 minutes at room temperature in the presence of cholesterol 3-sulfate at a predetermined concentration dissolved in DMSO or in the presence of DMSO alone (control) under the shielded condition from light, thereby preparing a pretreated substance of GEF. The concentration of DMSO was adjusted such that it became 3% (1% in the final reaction solution) in all samples.

Meanwhile, the prepared Rac was added to the reaction solution A at a concentration of 15 µM, and the solution was allowed to stand for 30 minutes on ice, thereby forming a GDP-Rac complex.

Bodipy-FL-GTP was added to the reaction solution A, which contained 100 µl, of the GDP-Rac complex prepared as above, such that the concentration thereof became 3.6 µM, and the solution was equilibrated for 3 minutes at 30° C. After the equilibration, 50 µl, of the pretreated GEF was added thereto, and a reaction was performed at 30° C.

During the reaction, the change in the fluorescence intensity of Bodipy-FL-GPT was monitored using a spectrofluorometer Enspire manufactured by PerkinElmer Inc (excitation wavelength: 488 nm, emission wavelength: 514 nm). By calculation, the values obtained by the measurement were corrected such that the fluorescence intensity became 0 at a reaction starting point (0 second).

Then, by using software (trade name "GraphPad Prism 5", manufactured by GraphPad Software Inc.), an approximation curve was created which is obtained in a case where the calculated corrected values are plotted on the y-axis and time (t) is plotted on the x-axis. The slope of the curve at t=0 to 10 seconds was adopted as the initial speed of the guanine nucleotide exchange reaction. By regarding the initial reaction speed of the control, to which only the vehicle (DMSO) was added, as 100%, the GEF activity (% activity) and the $IC_{50}$ value were calculated.

Figure 2:
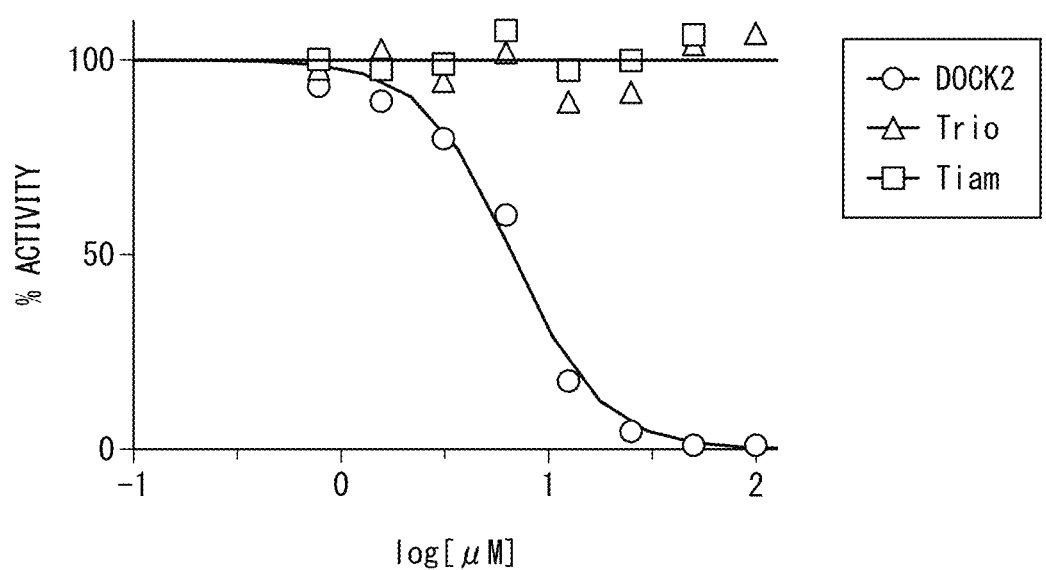
FIG. 2 is a graph showing the results of Experimental Example 1.

FIG. 2 is a graph showing the experiment results. As a result, it was revealed that cholesterol 3-sulfate specifically inhibits DOCK2-mediated Rac activation. The 50% inhibitory concentration ($IC_{50}$) of cholesterol 3-sulfate against DOCK2 was 6.7 µM. In contrast, $IC_{50}$ of cholesterol 3-sulfate against Trio and Tiam was higher than 300 µM, which showed that the GEF activity of these proteins was not affected at all.

Experimental Example 2

(Examination on Inhibition of DOCK2 Activity by Cholesterol 3-Sulfate)

An examination was performed using various steroid compounds to test their effects on the Rac activation induced by proteins composed of the lobe B and the lobe C of the DHR-2 domain of DOCK2.

As the steroid compounds, cholesterol 3-sulfate (hereinafter, referred to as "C3S" in some cases), cholesterol, cholesterol 3-acetate (hereinafter, referred to as "C3A" in some cases), pregnenolone 3-sulfate (hereinafter, referred to as "PREG3S" in some cases), dehydroepiandrosterone (hereinafter, referred to as "DHEA" in some cases), dehydroepiandrosterone 3-sulfate (hereinafter, referred to as "DHEA3S" in some cases), estrone 3-sulfate (hereinafter, referred to as "Estrone3S" in some cases), estriol 3-sulfate (hereinafter, referred to as "Estriol3S" in some cases), and estradiol 3-sulfate (hereinafter, referred to as "Estradiol3S" in some cases) were used.

More specifically, a DOCK2-DHR-2 domain protein prepared by the same method as described above was incubated for 20 minutes at room temperature in the presence of various steroid compounds at a predetermined concentration dissolved in DMSO or in the presence of DMSO alone (control) under the shielded condition from light, thereby preparing a pretreated substance of GEF. The concentration of DMSO was adjusted such that it became 3% (1% in the final reaction solution) in all samples. Then, by in-vitro GEF assay in which Rac and Bodipy-FL-GTP prepared by the same method as described above were used, Rac activation by the DHR-2 domain was measured.

(a) of FIG. 3 is a time-activity curve showing the results obtained by measuring the Rac activation in the presence of cholesterol 3-sulfate. (b) of FIG. 3 is a time-activity curve showing the results obtained by measuring the Rac activation in the presence of cholesterol. (c) of FIG. 3 is a time-activity curve showing the results obtained by measuring the Rac activation in the presence of cholesterol 3-acetate. FIG. 4 is a graph showing the results obtained by measuring the Rac activation in the presence of various steroid compounds at various concentrations. FIG. 5 is a graph showing the results obtained by comparing the Rac activation in the presence of various steroid compounds at 50 µM. In FIG. 5, "**" represents a significant difference p<0.01 in the t-test.

As a result, it was revealed that only cholesterol 3-sulfate specifically inhibits the Rac activation by the protein composed of the lobe B and the lobe C of the DHR-2 domain of DOCK2 at an $IC_{50}$ value of less than 10 µM. Table 1 shows the $IC_{50}$ values of various steroid compounds against the Rac activation by DOCK2DHR-2.

TABLE 1

| Steroid compound | $IC_{50}$ (µM) |
| --- | --- |
| C3S | 2.0 |
| C3A | >200 |
| Cholesterol | >200 |
| PREG3S | 76.6 |
| DHEA | >200 |
| DHEA3S | >200 |
| Estrone3S | >200 |

TABLE 1-continued

| Steroid compound | $IC_{50}$ (µM) |
| --- | --- |
| Estriol3S | >200 |
| Estradiol3S | >200 |

Experimental Example 3

(Detection of Specific Binding of DHR-2 Domain of DOCK2 to Cholesterol 3-Sulfate by ELISA Method)

By the ELISA method, the binding of various steroid compounds to a protein composed of the lobe B and the lobe C of the DHR-2 domain of DOCK2 was examined. As the steroid compounds, cholesterol 3-sulfate, cholesterol 3-acetate, cholesterol, pregnenolone 3-sulfate, estrone 3-sulfate, estriol 3-sulfate, estradiol 3-sulfate, dehydroepiandrosterone, and dehydroepiandrosterone 3-sulfate were used.

First, various steroid compounds prepared at 100 µg/ml by using 100% methanol were added in an amount of 50 µL to a 96-well plate for ELISA (trade name "Immulon 4HBX", Thermo Scientific) and immobilized for 1 hour in a clean bench by air drying. Subsequently, 5% bovine serum albumin (BSA) diluted with TBS (20 mM Tris-HCl-150 mM NaCl, pH 7.5) was added thereto in an amount of 180 µL, the steroid compounds were incubated for 6 hours at 4° C., and the wells were blocked.

Thereafter, each of the wells was rinsed three times with 180 µL of PBS-0.01% Tween-20. Then, the HIS-SUMO tagged protein composed of the lobe B and the lobe C of the DHR-2 domain of DOCK2 was added at a concentration of 2 µg/mL in an amount of 100 µL to the wells, and allowed to incubate for 2.5 hours at room temperature.

Then, each of the wells was rinsed three times with 180 µL of PBS-0.01% Tween-20. Subsequently, horseradish peroxidase (HRP)-labeled histidine probe (Thermo Scientific) diluted 5,000× was added in an amount of 100 µL to each well, and allowed to incubate for 1.5 hours at room temperature.

Thereafter, each of the wells was rinsed three times with 180 µL of PBS-0.01% Tween-20, a 3,3',5,5'-tetramethyl benzidine (TMB) solution (Thermo Scientific) as an HRP chromogenic substrate was added in an amount of 100 µL to each well so as to initiate a chromogenic reaction, and a stop solution (0.16 M sulfuric acid, Thermo Scientific) was added in an amount of 100 µL to each well so as to stop the reaction. Then, the absorbance at a wavelength of 450 nm was measured.

FIG. 6 is a graph showing the measurement results. In FIG. 6, "**" represents a significant difference p<0.01 in the t-test. As a result, it was revealed that the protein composed of the lobe B and the lobe C of the DHR-2 domain of DOCK2 specifically binds to cholesterol 3-sulfate.

Experimental Example 4

(Influence of Cholesterol 3-Sulfate on Binding of DHR-2 Domain of DOCK2 to Rac)

The influence of cholesterol 3-sulfate on the binding of the DHR-2 domain of DOCK2 to Rac was examined by pull-down assay using GST-Rac beads.

More specifically, first, E. coli strain induced to express GST-Rac by the same method as described above was subjected to ultrasonic disintegration, and the supernatant was mixed with Glutathione Sepharose 4B beads and incubated for 4 hours at 4° C. Then, the mixture was thoroughly rinsed with PBS-1 mM EDTA-0.01% Tween-20-5 mM 2-mercaptoethanol, thereby preparing GST-Rac-bonded beads.

Thereafter, 1 μg of a protein composed of the lobe B and the lobe C of the DHR-2 domain of DOCK2 was pretreated for 20 minutes at room temperature in 200 μL, of binding buffer (20 mM-Tris-HCl-150 mM NaCl-5 mM EDTA-0.01% Tween-20, pH 7.5) in the presence of 150 μM cholesterol 3-sulfate, cholesterol 3-acetate, cholesterol, and dehydroepiandrosterone 3-sulfate (DHEA3S) and in the presence of DMSO alone (control, final concentration 0.6%).

Then, 200 μL, of the binding buffer was added to the pretreated sample for dilution, and the diluted solution was added to 8 μL, of GST-Rac beads dispensed in advance to another tube in 200 μL, of the binding buffer (600 μL, in total). The solution was slowly mixed for 1 hour at 4° C. by using a rotator, and then the beads were rinsed three times by using 600 μL, of the binding buffer. The rinsed beads were added to 30 μL, of 1.5× sample buffer (87.5 mM-Tris-HCl (pH 6.8)-7.5% glycerol-2.5% SDS-0.003% bromophenol blue) and boiled for 5 minutes at 95° C.

As an input, 0.1 μg of a protein composed of the lobe B and the lobe C of the DHR-2 domain of DOCK2 was diluted with a 1× sample buffer and boiled in the same manner as described above. The sample was separated by SDS-PAGE, then transferred to a PVDF membrane, and blocked using 3% skimmed milk-TBST. Thereafter, the His-SUMO tagged DOCK2-DHR-2 protein bound to GST-Rac was detected by the Western blotting method, in which HRP-labeled histidine-tagged probe (Thermo Scientific) diluted 1,000× with 3% skimmed milk-TB ST was used.

FIG. 7 is a photograph showing the results obtained by detecting DOCK2-DHR-2 bound to GST-Rac beads by the Western blotting method. As a result, it was revealed that cholesterol 3-sulfate specifically inhibits the binding of DHR-2 to Rac.

Experimental Example 5

(Lymphocyte Migration Assay 1 Using Transwell)

The influence of cholesterol 3-sulfate on the migration of T cells was examined. As a control, an experiment using T cells derived from a DOCK2 knockout mouse was also performed. More specifically, first, mouse spleen cells ($1 \times 10^7$ cells/mL) were cultured for 1 hour at 37° C. in 0.5% BSA-containing RPMI-1640 (transwell medium) in the presence of cholesterol 3-sulfate at a predetermined concentration or in the presence of DMSO alone (control). The concentration of DMSO was adjusted such that the final concentration of DMSO became 0.2% in all samples.

Then, a transwell medium containing chemokine CCL21 (300 ng/mL) and cholesterol 3-sulfate at a predetermined concentration was added to a 24-well plate, and then a transwell (with 5 μm pores, Corning) was set in the well so as to load the pre-cultured cells ($1 \times 10^6$ cells/100 μL). Subsequently, the cells were incubated for 2 hours at 37° C., and the cells that moved to the lower chamber were collected and stained with PE-labeled anti Thy1.2-antibody ("53-2-1" model, BD Pharmingen). By dividing the number of Thy1.2-positive cells (T cells) in the lower chamber by the number of Thy1.2-positive cells (T cells) put into the transwell, the proportion of T cells having moved (migration of T cells (%)) was calculated.

FIG. 8 is a graph showing the results obtained by comparing T cell migration in response to CCL21 between wild-type and DOCK2-deficient mice. In FIG. 8, "" represents a significant difference p<0.01 in the t-test. FIG. 9 is a graph showing the results obtained by examining the inhibitory effect of cholesterol 3-sulfate on the T cell migration. In FIG. 9, "" represents a significant difference p<0.01 in the t-test. As a result, it was revealed that the migratory response of T cells is markedly inhibited by cholesterol 3-sulfate. Furthermore, it was revealed that in a case where cholesterol 3-sulfate was added at a concentration of 6.25 μM, the migration of T cells is inhibited to the level of T cells derived from DOCK2 knockout mouse.

Experimental Example 6

(Lymphocyte Migration Assay 2 Using Transwell)

The influence of various steroid compounds on the migration of T cells was examined. As the steroid compounds, cholesterol 3-sulfate, cholesterol, cholesterol 3-acetate, pregnenolone 3-sulfate, estrone 3-sulfate, estriol 3-sulfate, estradiol 3-sulfate, dehydroepiandrosterone, and dehydroepiandrosterone 3-sulfate were used.

More specifically, first, mouse spleen cells ($1 \times 10^7$ cells/mL) were cultured for 1 hour at 37° C. in 0.5% BSA-containing RPMI-1640 (transwell medium) in the presence of various steroid compounds at the concentration of 12.5 μM or in the presence of DMSO alone (control). The concentration of DMSO was adjusted such that the final concentration of DMSO became 0.2% in all samples.

Then, by performing the transwell assay as described above, the effects of various steroid compounds on the migratory responses of T cells to CCL21 (300 ng/mL) were examined by comparison.

FIG. 10 is a graph showing the results obtained by examining the effects of various steroid compounds on the migration of lymphocytes. In FIG. 10, "**" represents a significant difference p<0.01 in the t-test. As a result, it was revealed that only cholesterol 3-sulfate specifically inhibits the migration of T cells.

Experimental Example 7

(Neutrophil Migration Assay 1)

The influence of cholesterol 3-sulfate on a migration speed of neutrophils was examined. More specifically, in the presence of cholesterol 3-sulfate at a predetermined concentration or in the presence of DMSO alone (vehicle control), neutrophils isolated from the mouse bone marrow were incubated for 1 hour at room temperature in 20 mM HEPES-NaOH (pH 7.3)-0.1% BSA-containing RPMI-1640 (Taxiscan medium). The concentration of DMSO was adjusted such that the final concentration of DMSO became 0.2% in all samples.

Then, the pre-treated cells were loaded on wells of one side of the chamber of EZ-TAXIScan (Effector Cell Institute, Inc). After 1 μL of fMLP in a Taxiscan medium was added at a concentration of 10 μM to wells of the other side 260 μm distant from the above wells, neutrophils were allowed to migrate in the presence of a fMLP gradient (0 to 10 μM). Phase-contrast micrographs were obtained for 20 minutes at an interval of 30 seconds, and the trace and speed of neutrophils were analyzed by using manual tracking of the Image J program and a chemotaxis and migration tool.

(a) and (b) of FIG. 11 are graphs showing the experiment results obtained by examining the effect of cholesterol 3-sulfate on neutrophil chemotaxis in response to fMLP. (a) of FIG. 11 shows the migration speed, and (b) of FIG. 11 shows the trace of migrating neutrophils. In (a) of FIG. 11, "**" represents a significant difference p<0.01 in the t-test.

As a result, it was revealed that the migration of neutrophils is markedly inhibited by cholesterol 3-sulfate.

Experimental Example 8

(Neutrophil Migration Assay 2)

An examination was performed about the influence of cholesterol 3-sulfate on the migration speed of neutrophils when the cells and the chemical migration factor (fMLP) are added to the same well without pretreating the cells. More specifically, neutrophils derived from the mouse bone marrow were loaded on wells of one side of the chamber of EZ-TAXIScan (Effector Cell Institute, Inc), and 1 μL of cholesterol 3-sulfate, dehydroepiandrosterone 3-sulfate, or DMSO (control, final concentration 3%) was added at the concentration of 150 μM to the well containing 3 μM of fMLP solution, which was located on the other side 260 μm distant from the above wells, and neutrophils were allowed to migrate. Phase-contrast micrographs were obtained for 40 minutes at an interval of 30 seconds and analyzed by the same method as described above.

(a) to (c) of FIG. 12 are graphs and photographs showing the experiment results. The upper portion shows graphs showing a relationship between the position of the neutrophils and the migration speed in an area from the starting point (wells on which the neutrophils were loaded) to an end point (wells to which fMLP and various steroids were added) of the chamber of the EX-TAXIScan. The middle portion shows phase-contrast micrographs of neutrophils migrating under the respective conditions at each point in time. The lower portion shows graphs showing the trace of the migrating neutrophils. (a) of FIG. 12 shows the results obtained when DMSO was added to the fMLP source. (b) of FIG. 12 shows the results obtained when cholesterol 3-sulfate was added to the fMLP source. (c) of FIG. 12 shows the results obtained when dehydroepiandrosterone 3-sulfate was added to the fMLP source.

As a result, it was revealed that the migrating neutrophils rapidly stop at a point where the concentration of cholesterol 3-sulfate reaches a predetermined level. This effect is specific to cholesterol 3-sulfate.

Experimental Example 9

(Lymphocyte Migration Assay on Stroma Cells)

The migratory properties of T cells on stroma cells overexpressing Sult2B1b, an enzyme producing cholesterol 3-sulfate, were examined. More specifically, a secondary lymphoid tissue was extracted from a mouse and shredded. After the tissue was suspended in a DMEM medium, 1 mg/mL collagenase D (Roche Diagnostics), 0.8 mg/mL dispase (Roche Diagnostics), and 0.1 mg/mL DNase 1 were added to the samples, and treated for 45 minutes at 37° C. to separate the stroma cells.

The separated stroma cells were cultured in 10% FBS-DMEM. On the $5^{th}$ day after the start of culture, hematopoietic-lineage cells including the remaining lymphocytes were removed with the microbeads (Miltenyi Biotec) coated with anti-CD45 antibodies, and the stroma cells were newly seeded in a glass bottom dish ($4 \times 10^4$ cells/dish). The cells were infected with the retrovirus consecutively on the $6^{th}$, $7^{th}$, and $8^{th}$ days after the start of culture so as to perform gene introduction. For obtaining the retrovirus for infection, pMX-IRES-GFP (control) or pMX-SULT2B1b-IRES-GFP was transfected into a packaging cell line Plat-E, and the culture supernatant containing recombinant virus was directly used. On the $9^{th}$ day of culture, the cells were stimulated with TNF-α (10 ng/mL), and on the $10^{th}$ day, assay was performed by adding CCL21 (300 ng/mL) thereto.

During the assay, T cells isolated from the mouse spleen by using a PanT isolation kit (Miltenyi Biotec) were seeded on the stroma cells, the dish was set in a fluorescence microscope with a stage with a heat-retaining function. While being incubated at 37° C. in the presence of $CO_2$, the T cells were allowed to migrate, and differential interference contrast micrographs and fluorescence micrographs were obtained for 20 minutes at an interval of 1 minute. The stacks of the captured images were reproduced, and the number of GFP-positive stroma cells on which the T cells migrated was counted and divided by the total number of the GFP-positive stroma cells, thereby calculating the migration properties of the T cells (% stroma cells).

(a) of FIG. 13 shows time-lapse images showing the migratory properties of the T cells on the stroma cells expressing GFP alone as a control or those expressing the Sult2B1b gene and GFP. (b) of FIG. 13 is a graph showing the results obtained by comparing the migratory properties of the T cells on the stroma cells expressing GFP alone as a control or those expressing the Sult2B1b gene and GFP. In (b) of FIG. 13, "**" represents a significant difference $p<0.01$ in the t-test.

As a result, it was revealed that on the stroma cells expressing the Sult2B1b enzyme, T cells cannot pass on the stroma cells and stay in the peripheral site. This result supports a theory that the migration of lymphocytes is inhibited and hence immune evasion occurs, around the cells producing cholesterol 3-sulfate.

Experimental Example 10

(Examination on Expression of Sult2B1b Protein in Each Tissue of Mouse)

The Sult2B1b protein and the Sult2B1a protein are formed from the same gene through RNA splicing, resulting in different amino acid sequences in the N-terminal region between them. For producing cholesterol 3-sulfate, the expression of the Sult2B1b protein is essential. Therefore, the antibody specific to the Sult2B1b protein was developed, and the expression of the Sult2B1b protein in each tissue of a mouse was examined by the Western blotting method.

Specifically, proteins extracted from each tissue of a mouse were separated by SDS-PAGE, then transferred to a PVDF membrane, and detected with antibodies specific to a mouse Sult2B1b protein. (a) of FIG. 14 shows photographs showing the results detected by the Western blotting method. As a loading control, an actin protein was used. The total amount of proteins applied to each lane was 20 μg. As a result, it was revealed that the Sult2B1b protein is expressed most abundantly in the Harderian gland, which provides the lipid components of tears. Furthermore, it was confirmed that the Sult2B1b protein is also expressed in the small intestine and the skin.

Subsequently, the same examination was performed using each tissue of an Sult2B1b protein-deficient mouse. (b) of FIG. 14 is photograph showing the results obtained by detecting the expression of the Sult2B1b protein in each of the tissues of a wild-type mouse (+/+) and an Sult2B1b gene knockout mouse (−/−). As a loading control, an actin protein was used. The total amount of proteins applied to each lane was 20 μg. As a result, it was confirmed that the Sult2B1b protein is not expressed in the Sult2B1b gene knockout mouse.

Experimental Example 11

(Examination on Amount of Cholesterol 3-Sulfate Present in Each Tissue of Mouse)

Cholesterol 3-sulfate (C3S) in each tissue and tear of a wild-type mouse (+/+) and a Sult2B1b gene knockout mouse (−/−) was quantified by mass spectrometry (n 7). Specifically, deuterium-labeled cholesterol 3-sulfate was added as an internal standard to each tissue, followed by homogenization. Thereafter, the suspension of each tissue was subjected to ultrafiltration by using an ultrafiltration tube, and the filtrate was directly analyzed by LC-MS/MS. The absolute amount of cholesterol 3-sulfate was calculated based on a ratio of a peak area of cholesterol 3-sulfate to a peak area of the internal standard. (a) and (b) of FIG. 15 are graphs showing the results obtained by quantifying cholesterol 3-sulfate.

As a result, it was revealed that in the wild-type mouse, cholesterol 3-sulfate is abundantly produced in the Harderian gland and tears, consistent with the strong expression of Sult2B1b protein in the Harderian gland. Furthermore, it was confirmed that cholesterol 3-sulfate is also present in the small intestine and the skin. In contrast, it was confirmed that in the Sult2B1b gene knockout mouse (−/−), the present of cholesterol 3-sulfate is not detected.

Subsequently, by using a mass spectrometric microscope, the localization of cholesterol 3-sulfate in the eyeballs of the wild-type mouse (+1+) and the Sult2B1b gene knockout mouse (−/−) was visualized.

Specifically, each of the mouse samples was frozen, and then fresh frozen thin sections were prepared. As a matrix, 9-amino acridine was sprayed onto each of the sections, and the sections were measured using the mass spectrometric microscope. From the data obtained by measurement, a peak that appeared at a mass-to-charge ratio (m/z)=465 was identified as cholesterol 3-sulfate by tandem mass spectrometry, and the peak intensity distribution thereof was made into an image. Then, the sections having undergone measurement were subjected to hematoxylin-eosin (HE) staining and observed using an optical microscope.

FIG. 16 shows mass spectrometric micrographs and optical micrographs showing the localization of cholesterol 3-sulfate in the eyeballs of mice. The upper left image is a mass spectrometric micrograph showing the localization of cholesterol 3-sulfate in an eyeball of the wile-type mouse (+/+). The bar represents 500 μm. The lower left image is an optical micrograph corresponding to the field of view of the upper left image. The upper right image is a mass spectrometric micrograph showing the localization of cholesterol 3-sulfate in an eyeball of the Sult2B1b gene knockout mouse (−/−). The lower right image is an optical micrograph corresponding to the field of view of the upper right image.

As a result, it was revealed that in the wild-type mice, a relatively large amount of cholesterol 3-sulfate is also present in the anterior chamber of the eyeball.

Experimental Example 12

(Examination 1 on Role of Cholesterol 3-Sulfate in Ocular Inflammation)

As a result of analyzing UV-induced photokeratitis in Sult2B1b gene heterozygous mice (+/−) and Sult2B1b gene knockout mice (−/−), atrophy of the corneal epithelial layer was comparably observed in both mice. Therefore, the eyeball section of each of the mice was subjected to hematoxylin-eosin (HE) staining and observed using an optical microscope.

(a) of FIG. 17 shows the micrographs of eyeball sections of the mice. (b) of FIG. 17 is a graph showing the results obtained by measuring the total number of inflammatory cells infiltrating into the anterior chamber of eye of the mice before UV irradiation (−) and after UV irradiation (+). (c) of FIG. 17 shows fluorescence micrographs showing the results obtained by immunostaining of the eyeball sections of using an antibody for Gr1, a marker for neutrophils. The dotted line in the photographs shows the boundary of the cornea.

As a result, it was revealed that in the eyeball of the Sult2B1b gene knockout mice (−/−), the infiltration of the inflammatory neutrophils into the anterior chamber of eye is further accelerated after UV irradiation than in the heterozygous mice (+/−).

Thereafter, cholesterol 3-sulfate was applied to the eyes of the Sult2B1b gene knockout mouse (−/−) before and after UV irradiation, and the total number of inflammatory cells infiltrating the anterior chamber of eye was counted. As a control, mouse for whom only a vehicle was applied to its eyes was used.

(d) of FIG. 17 is a graph showing the results obtained by counting the total number of inflammatory cells infiltrating into the anterior chamber of eye of Sult2B1b gene knockout mice (−/−). As a result, it was revealed that the UV irradiation-induced infiltration of the inflammatory cells into the anterior chamber of eye is inhibited when eye drops of cholesterol 3-sulfate were administered to Sult2B1b gene knockout mice.

Experimental Example 13

(Examination 2 on Role of Cholesterol 3-Sulfate in Ocular Inflammation)

An examination was performed on conjunctivitis models induced by sensitizing Sult2B1b gene hetero-type mice (+/−) and Sult2B1b gene knockout mice (−/−) with ragweed pollen and topically challenged with the same antigen at 10 and 12 days later. The eyeball section of each category of the mice was subjected to hematoxylin-eosin (HE) staining and observed using an optical microscope.

(a) of FIG. 18 shows the micrographs of the eyeball sections of the mice. (b) of FIG. 18 is a graph showing the results obtained by counting the total number of inflammatory cells infiltrating into the conjunctiva of the mice.

As a result, it was revealed that in the conjunctivitis models induced by the ragweed pollen, the infiltration of inflammatory cells into the conjunctiva is further accelerated in the eyeball of the Sult2B1b gene knockout mice (−/−) than in the heterozygous mice (+/−).

Thereafter, the Sult2B1b gene knockout mice (−/−) were exposed to ragweed pollen, and cholesterol 3-sulfate was applied into the eyes of the mice before and after the topical challenge with ragweed pollen. Then, the total number of inflammatory cells infiltrating into the conjunctiva was counted. As a control, a mouse for whom only a vehicle was applied into its eyes was used.

(c) of FIG. 18 is a graph showing the results obtained by counting the total number of inflammatory cells infiltrating into the conjunctiva of the mice. As a result, it was revealed that the infiltration of the inflammatory cells into the conjunctiva in response to ragweed pollen is further inhibited by the application of cholesterol 3-sulfate to the eyes.

Experimental Example 14

(Detection 1 of Cholesterol 3-Sulfate)

By using a mass spectrometric microscope, the distribution of cholesterol 3-sulfate in an embryonic tissue of a pregnant mouse was detected. More specifically, an embryo (E 8.5) of a wild-type pregnant mouse was isolated from the pregnant mother and frozen, and then a fresh frozen thin section was prepared. As a matrix, 9-amino acridine was sprayed onto the section, and the section was measured using a mass spectrometric microscope. From the data obtained by measurement, a peak that appeared at a mass-to-charge ratio (m/z)=465 was identified as cholesterol 3-sulfate by tandem mass spectrometry, and the peak intensity distribution thereof was made into an image. Then, the section having undergone measurement was subjected to hematoxylin-eosin (HE) staining.

(a) of FIG. 19 is an HE staining image of the wild-type mouse embryo section. (b) of FIG. 19 is a photograph showing the distribution of cholesterol 3-sulfate (m/z=465) in the same section. (c) of FIG. 19 is an image obtained by overlapping (a) and (b) of FIG. 19. As a result, it was revealed that cholesterol 3-sulfate is localized in the vicinity of the embryo. This result indicates a possibility that cholesterol 3-sulfate is important for forming an immune-privileged site during pregnancy.

Experimental Example 15

(Detection 2 of Cholesterol 3-Sulfate)

By using a liver metastasis mouse model of human colorectal cancer, the distribution of cholesterol 3-sulfate in a cancer tissue was detected using a mass spectrometric microscope. More specifically, a human colorectal cancer cell strain HCT116 (HCT116/venus) cells were fluorescently labeled by expressing a venus gene (a GFP mutant), and was introduced into the spleen of an NOG mouse (NOD/Shi-scid/IL-2RyKO mouse). After 2 weeks, the liver of the NOG mouse was extracted and frozen with liquid nitrogen. Then, a frozen section was prepared and observed using a fluorescence microscope. Subsequently, as a matrix, 9-amino acridine was sprayed onto the section to be tested, and the section was measured using a mass spectrometric microscope. From the data obtained by measurement, a peak that appeared at m/z=465 was identified as cholesterol 3-sulfate by tandem mass spectrometry, and the peak intensity distribution thereof was made into an image.

(a) of FIG. 20 is a fluorescence micrograph showing a metastasis lesion of HCT116/venus cells in the liver tissue. (b) of FIG. 20 is a mass spectrometric micrograph showing the distribution of cholesterol 3-sulfate. (c) of FIG. 20 is an image obtained by overlapping (a) and (b) of FIG. 20. As a result, it was revealed that the cancer tissue metastasizing to the liver highly expresses cholesterol 3-sulfate. This result supports the theory that cholesterol 3-sulfate is important for forming an immune-privileged site through which cancer cells escape from the immune surveillance mechanism of the host.

Experimental Example 16

(Detection 3 of Cholesterol 3-Sulfate)

By using a subcutaneous transplantation model of human non-small cell lung cancer cells, the distribution of cholesterol 3-sulfate and arachidonic acid in a subcutaneous tumor tissue was detected using a mass spectrometric microscope. More specifically, a human non-small cell lung cancer cell strain PC-9 was subcutaneously transplanted to nude mice. After 4 weeks, the subcutaneous tumor was extracted, subjected to HE staining, and analyzed using a mass spectrometric microscope. Specifically, as a matrix, 9-amino acridine was sprayed onto the section to be tested, and the section was measured using a mass spectrometric microscope. From the data obtained by measurement, a peak that appeared at m/z=465 was identified as cholesterol 3-sulfate by tandem mass spectrometry, and the peak intensity distribution thereof was made into an image. Subsequently, the section having undergone measurement was subjected to hematoxylin-eosin (HE) staining.

(a) of FIG. 21 is a micrograph showing the HE staining of the tumor subcutaneously transplanted into a nude mouse. (b) of FIG. 21 is a mass spectrometric micrograph showing the distribution of cholesterol 3-sulfate and arachidonic acid, the latter of which is a marker for the infiltration of immune cells, in the tissue. As a result, it was revealed that cholesterol 3-sulfate is localized in the vicinity of the cancer tissue. Furthermore, cholesterol 3-sulfate and arachidonic acid were exclusively localized. This result shows that immune cells cannot infiltrate the region where cholesterol 3-sulfate is present. This result further supports the theory that cholesterol 3-sulfate is important for forming an immune-privileged site through which cancer cells escape from the immune surveillance mechanism of the host.

INDUSTRIAL APPLICABILITY

According to the present invention, a novel immunoregulatory agent can be provided. In a case where the immunoregulatory agent of the present invention is used as an immunoregulatory agent as an aspect thereof, it is possible to inhibit inflammatory diseases such as autoimmune diseases resulting from excessive immune responses. In another aspect, in a case where the immunoregulatory agent of the present invention is used as an immune privilege-removing agent, it is possible to cancel the immune evasive environments in cancers and to stimulate the immune response against cancer. Furthermore, the use of the immunoregulatory agent of the present invention can make a contribution to regenerative medicine or transplantation medicine, by artificially creating an immune-privileged site and inhibiting a rejection reaction to a graft.

---

The invention claimed is:

1. A method for regulating Rac-activating activity of DOCK2, the method comprising at least one of:
   (i) forming an immune-privileged site by administering to a patient in need of treatment an effective amount of cholesterol 3-sulfate, a pharmacologically acceptable salt thereof, or a solvate thereof, to regulate DOCK2-mediated Rac activation;
   (ii) forming an immune-privileged site by administering to a patient in need of treatment an effective amount of a SULT2B1b protein, or an expression vector of the SULT2B1b protein; and
   (iii) destroying an immune-privileged site by administering to a patient in need of treatment an effective amount of an expression inhibition substance of the SULT2B1b protein,
   wherein:
   the SULT2B1b protein is a protein which comprises the amino acid sequence of SEQ ID NO: 2, or a protein which comprises an amino acid sequence formed by the deletion, substitution, or addition of 1 to 3 amino acids in the amino acid sequence of SEQ ID NO: 2, and acts to add a sulfonic acid group to the carbon at position 3 of cholesterol and generate cholesterol 3-sulfate, and
   the expression inhibition substance of the SULT2B1b protein is siRNA or shRNA.

2. The method for regulating Rac-activating activity of DOCK2 according to claim 1, wherein:
   forming the immune-privileged site includes inhibiting Rac-activating activity of DOCK2, and
   infiltration of immune cells is suppressed in the immune-privileged site.

3. The method for regulating Rac-activating activity of DOCK2 according to claim 1, wherein destroying the immune-privileged site includes accelerating Rac-activating activity of DOCK2.

4. The method for regulating Rac-activating activity of DOCK2 according to claim 1, wherein the SULT2B1b protein is a protein which comprises the amino acid sequence of SEQ ID NO: 2.

5. The method for regulating Rac-activating activity of DOCK2 according to claim 1, the method comprising:
   forming an immune-privileged site by administering to the patient an effective amount of the cholesterol 3-sulfate, a pharmacologically acceptable salt thereof, or a solvate thereof, to regulate DOCK2-mediated Rac activation.

6. The method for regulating Rac-activating activity of DOCK2 according to claim 1, the method comprising:
   forming an immune-privileged site by administering to the patient an effective amount of the SULT2B1b protein, or an expression vector of the SULT2B1b protein.

7. The method for regulating Rac-activating activity of DOCK2 according to claim 1, the method comprising:
   destroying an immune-privileged site by administering to the patient an effective amount of the expression inhibition substance of the SULT2B1b protein.

8. The method for regulating Rac-activating activity of DOCK2 according to claim 7, wherein the expression inhibition substance of the SULT2B1b protein is siRNA, and sense strand of the siRNA has a base sequence selected from the group consisting of SEQ ID NOS: 4 to 7.

9. The method for regulating Rac-activating activity of DOCK2 according to claim 7, wherein the expression inhibition substance of the SULT2B1b protein is shRNA, and the shRNA has a base sequence selected from the group consisting of SEQ ID NOS: 8 to 10.

* * * * *